United States Patent
Kohara

(10) Patent No.: US 9,715,745 B2
(45) Date of Patent: Jul. 25, 2017

(54) X-RAY CT APPARATUS AND IMAGE RECONSTRUCTION METHOD

(71) Applicant: HITACHI, LTD., Tokyo (JP)

(72) Inventor: Ryota Kohara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 100 days.

(21) Appl. No.: 14/759,480

(22) PCT Filed: Jan. 29, 2014

(86) PCT No.: PCT/JP2014/051926
§ 371 (c)(1),
(2) Date: Jul. 7, 2015

(87) PCT Pub. No.: WO2014/123041
PCT Pub. Date: Aug. 14, 2014

(65) Prior Publication Data
US 2015/0348291 A1    Dec. 3, 2015

(30) Foreign Application Priority Data

Feb. 5, 2013   (JP) .................................. 2013-020456

(51) Int. Cl.
*G06K 9/00* (2006.01)
*G06T 11/00* (2006.01)
(Continued)

(52) U.S. Cl.
CPC ............ *G06T 11/005* (2013.01); *A61B 6/032* (2013.01); *A61B 6/5205* (2013.01);
(Continued)

(58) Field of Classification Search
CPC ......... A61B 6/032; A61B 6/469; A61B 6/481; A61B 6/5205; A61B 6/5258; A61B 6/541;
(Continued)

(56) References Cited

U.S. PATENT DOCUMENTS 9,123,098 B2 *  9/2015  Takahashi .............. A61B 6/032
2004/0022447 A1   2/2004  Mukhopadhyay et al.
(Continued)

FOREIGN PATENT DOCUMENTS

JP    2003-153893    5/2003
JP    2004-72767     3/2004
(Continued)

OTHER PUBLICATIONS

International Search Report in corresponding International application No. PCT/JP2014/051926.
(Continued)

*Primary Examiner* — Tom Y Lu
(74) *Attorney, Agent, or Firm* — Cooper & Dunham LLP

(57) ABSTRACT

To provide an X-ray CT apparatus that can reduce calculation time required for an iterative approximation projection data correction process by restricting a range for the iterative approximation projection data correction process and generate low-noise images according to the examination purpose, the calculation device of the X-ray CT apparatus generates correction projection data by performing an iterative approximation projection data correction process for projection data acquired in scanning and reconstructs CT images using the correction projection data. The calculation device determines a range to which iterative approximation projection data correction process is applied based on scanning conditions and reconstruction conditions. For example, a slice direction application range is determined based on an X-ray beam width, and a channel direction application range is determined based on an FOV. The calculation device performs an iterative approximation projection data correction process for projection data corresponding to the determined application range to generate correction projection data.

13 Claims, 27 Drawing Sheets

(51) Int. Cl.
  *G06T 5/00* (2006.01)
  *G06T 7/00* (2017.01)
  *A61B 6/03* (2006.01)
  *A61B 6/00* (2006.01)

(52) U.S. Cl.
  CPC ............ *A61B 6/5258* (2013.01); *G06T 5/002* (2013.01); *G06T 7/0012* (2013.01); *A61B 6/469* (2013.01); *A61B 6/481* (2013.01); *A61B 6/541* (2013.01); *G06T 2207/10081* (2013.01); *G06T 2207/10116* (2013.01); *G06T 2207/20104* (2013.01); *G06T 2207/30004* (2013.01); *G06T 2211/40* (2013.01); *G06T 2211/424* (2013.01); *G06T 2211/428* (2013.01)

(58) Field of Classification Search
  CPC ......... G06T 11/005; G06T 2207/10081; G06T 2207/10116; G06T 2207/20104; G06T 2207/30004; G06T 2211/40; G06T 5/002; G06T 7/0012; G06T 2211/424; G06T 2211/428
  See application file for complete search history.

(56) References Cited

U.S. PATENT DOCUMENTS

| 2007/0167730 | A1 | 7/2007 | Tatebayashi |
| 2009/0190814 | A1 | 7/2009 | Bouman et al. |
| 2011/0142315 | A1* | 6/2011 | Hsieh .................... A61B 6/032 382/131 |
| 2014/0226887 | A1 | 8/2014 | Takahashi et al. |

FOREIGN PATENT DOCUMENTS

| JP | 2007-144144 | 6/2007 |
| JP | 2009-87270 | 4/2009 |
| JP | 2009-172380 | 8/2009 |
| JP | 2011-36300 | 2/2011 |
| JP | 2011-152255 | 8/2011 |
| WO | WO2012/147471 A1 | 11/2012 |

OTHER PUBLICATIONS

J. Wang et al., "Penalized Weighted Least-Squares Approach to Sinogram Noise Reduction and Image Reconstruction for Low-Dose X-Ray Computer Tomograpy", IEEE Transactions on Medical Imaging, vol. 25, No. 10, Oct. 2006.

* cited by examiner

X-RAY CT APPARATUS AND IMAGE RECONSTRUCTION METHOD

TECHNICAL FIELD

The present invention relates to an X-ray CT apparatus etc. that obtain CT images by irradiating an X-ray to an object. In particular, the invention relates to a technique in which an X-ray CT apparatus executes projection data correction at a high speed by the iterative approximation method.

BACKGROUND ART

In order to perform CT examination with less exposure dose, an X-ray CT apparatus executing image reconstruction by the iterative approximation method has been developed in recent years. The image reconstruction by the iterative approximation method can obtain CT images with less noise even at a low dose of radiation.

In the non-patent literature 1, an iterative approximation projection data correction process that is one of the iterative approximation methods is disclosed. An iterative approximation projection data correction process is one projection data correction process that is preprocessing of image reconstruction. In an iterative approximation projection data correction process, an update formula in which a projection value of projection data is a variable is used. The update formula includes a smoothing coefficient (referred to also as a correction coefficient or a penalty item) showing a correction intensity. Also, the update formula includes weighting addition processing between adjacent elements. In an iterative approximation projection data correction process, the above update formula is used to update a projection value repeatedly. Then, for each update, a projection value obtained after the update is evaluated using a cost function. Until the cost function result becomes satisfactory, projection value update is repeated for each detection element.

The formula (1) shows a cost function to be used in conventional an iterative approximation projection data correction process.

The formula (2) shows an update formula to be used in conventional an iterative approximation projection data correction process.

$$\Phi(q) = \sum_i d_i(y_i - p_i)^2 + \beta \sum_i \sum_{m \in N_i} w_{im}(p_i - p_m)^2 \quad (1)$$

$$p_i^{(n+1)} = \frac{y_i + \frac{\beta}{d_i}\left(\sum_{m \in N_i^1} w_{im} p_m^{(n+1)} + \sum_{m \in N_i^2} w_{im} p_m^{(n)}\right)}{1 + \frac{\beta}{d_i} \sum_{m \in N_i} w_{im}} \quad (2)$$

In the above formulas (1) and (2), "p" is an updated projection value, "y" is an original projection value, "β" is a smoothing coefficient, "d" is a detection characteristic value, "i" is a detection element number, "n" is a repetition number, and "w" is a weight.

Additionally, the respective formulas corresponding to the above formulas (1) and (2) are described in the non-patent literature 1. The formula (1) corresponds to the formula (9) described on p. 1274 of the non-patent literature 1. The formula (2) corresponds to the formula (11) described on p. 1274 of the non-patent literature 1.

In the present invention, although the respective formulas are described using a different form and different symbols from the non-patent literature 1 so that the explanation is made along the main aim of the invention, the contents of the above formulas (1) and (2) are the same as the respective formulas described in the non-patent literature 1.

CITATION LIST

Non-Patent Literature

NPTL 1: Jing Wang et al., "Penalized Weighted Least-Squares Approach to Sinogram Noise Reduction and Image Reconstruction for Low-Dose X-Ray Computed Tomography", IEEE TRANSACTIONS ON MEDICAL IMAGING, VOL. 25, NO. 10, October 2006, 1272-1283

SUMMARY OF INVENTION

Technical Problem

However, in the process described in the above non-patent literature 1, an iterative approximation projection data correction process is applied to all the detection elements. Therefore, there is a problem that it requires an enormous time to process.

The present invention was made in light of the above problems, and the purposes are to reduce a calculation time required for an iterative approximation projection data correction process by limiting an application range for an iterative approximation projection data correction process and to provide an X-ray CT apparatus etc. capable of generating low-noise images according to the examination purpose.

Solution to Problem

In order to achieve the above purposes, the X-ray CT apparatus of the present invention is comprised of an X-ray generating device irradiating an X-ray from the surroundings of an object; an X-ray detection device detecting an X-ray transmitted through the object; a data collection device collecting data detected by the X-ray detection device; an calculation device generating projection data by inputting data to be collected by the data collection device and reconstructing a CT image using the projection data; and a display device displaying the CT image, and the calculation device is comprised of an application range determining unit determining an application range for an iterative approximation projection data correction process that is a correction process by the iterative approximation method which uses a smoothing coefficient showing a correction intensity for the projection data; a an iterative approximation projection data correction processing unit performing the iterative approximation projection data correction process for projection data that corresponds to the range determined by the application range determining unit to generate correction projection data; and an image reconstruction unit reconstructing a CT image using the correction projection data.

Also, the image reconstruction method of the present invention performs correction processing by the iterative approximation method for projection data using a smoothing coefficient showing a correction intensity to generate correction projection data, reconstructs a CT image using the correction projection data, and then performs a application range determining step in which an calculation device determines a range to apply correction processing by the said iterative approximation method for the projection data and a correction projection data generating step performing correction processing by the said iterative approximation method for projection data that corresponds to the determined range to generate correction projection data.

Advantageous Effects of Invention

According to the present invention, by limiting an application range for an iterative approximation projection data correction process, a calculation time required for an iterative approximation projection data correction process can be reduced, and an X-ray CT apparatus etc. capable of generating low-noise images according to the examination purpose can be provided.

DESCRIPTION OF EMBODIMENTS

Figure 1:
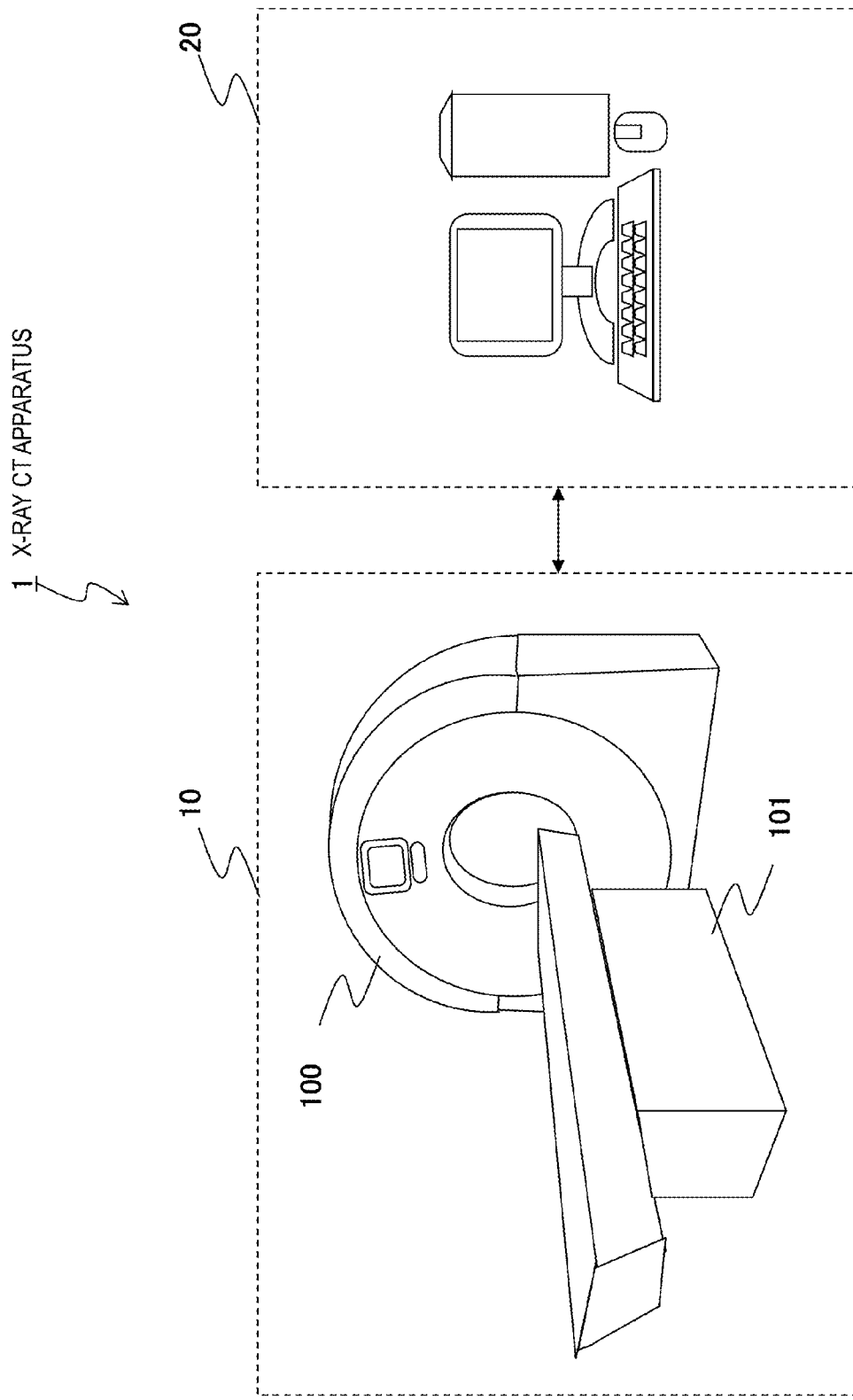
FIG. 1 is an outside view showing the overall configuration of the X-ray CT apparatus 1.

Hereinafter, the suitable embodiments of the present invention will be described in detail based on diagrams. First, referring to FIGS. 1 and 2, the hardware configuration of the X-ray CT apparatus 1 will be described.

The X-ray CT apparatus 1 is generally comprised of the scanner 10 and the operation unit 20.

The scanner 10 includes the bed device 101, the X-ray generating device 102, the X-ray detection device 103, the collimator device 104, the high-voltage generating device 105, the data collection device 106, the driving device 107, etc. the operation unit 20 includes the central control device 200, the input/output device 201, the calculation device 202, etc.

An operator inputs scanning conditions, reconstruction conditions, etc. via the input/output device 201. The scanning conditions are, for example, an X-ray beam width, a bed sending speed, a tube current, a tube voltage, a scanning range (range in the body-axis direction), the number of scanning views per rotation, etc. Also, the reconstruction conditions, for example, are a region of interest, an FOV (field of view), a reconstruction filter function, etc. The input/output device 201 includes the display device 211 displaying a CT image etc., the input device 212 such as a mouse, a trackball, a keyboard, and a touch panel, the storage device 213 storing data, etc.

The central control device 200 inputs the scanning conditions and reconstruction conditions and transmits a control signal required for scanning to the respective devices included in the scanner 10. The collimator device 104 controls its position based on the control signal. When scanning starts after receiving a scanning start signal, the high-voltage generating device 105 applies a tube voltage and a tube current to the X-ray generating device 102 based on a control signal. In the X-ray generating device 102, electrons of energy according to the applied tube voltage are emitted from a cathode, the emitted electrons collide strike a target (an anode), and then an X-ray of energy according to the electronic energy is irradiated to the object 3.

The driving device 107 rotates the gantry 100 in which the X-ray generating device 102, the X-ray detection device 103, etc. are installed around the object 3 based on a control signal. The bed device 101 controls a bed based on the control signal.

An irradiation range of an X-ray irradiated from the X-ray generating device 102 is limited by a collimator. The X-ray is absorbed (attenuated) according to the X-ray absorption coefficient in each tissue in the object 3, passes through the object 3, and then is detected by the X-ray detection device 103 disposed in the position opposite to the X-ray generating device 102. The X-ray detection device 103 is comprised of a plurality of detection elements arranged in the two-dimensional direction (a channel direction and the column direction orthogonal to this). The X-ray received by each detection element is converted into real projection data. That is, the data collection device 106 performs various data processes (such as changing to digital data, LOG conversion, and calibration) for the X-ray detected by the X-ray detection device 103, and the X-ray is collected as raw data to be input in the calculation device 202.

At this time, because the X-ray generating device 102 and the X-ray detection device 103 facing each other rotate around the object 3, the X-ray generating device 102 is to irradiate an X-ray from the surroundings of the object 3. Also, the X-ray detection device 103 is to detect an X-ray transmitted through the object 3. That is, the raw data is collected in the rotation direction at discrete positions of the X-ray tube (the detector position opposite to the X-ray tube). The acquisition unit of the projection data at each position of the X-ray tube is referred to as "view".

The calculation device 202 is comprised of the reconstruction processing device 221, the image processing device 222, etc. The input/output device 201 includes the input device 212, the display device 211, the storage device 213, etc.

The reconstruction processing device 221 generates projection data by inputting raw data to be collected by the data collection device 106. Also, the reconstruction processing device 221 performs an iterative approximation projection data correction process for the projection data to generate correction projection data. Then, CT images are reconstructed using the correction projection data.

Additionally, the present invention relates to the improvement of an iterative approximation projection data correction process. The iterative approximation projection data correction process related to the present invention will be described later.

The reconstruction processing device 221 stores the generated CT images in the storage device 213. Also, the reconstruction processing device 221 displays a generated CT image on the display device 211. Alternatively, the image processing device 222 performs image processing for CT images to be stored in the storage device 213 and displays CT images after image processing on the display device 211.

In the X-ray CT apparatus 1, there are multi-slice CT that uses the X-ray detection device 103 where detection elements are arranged in the two-dimensional direction and single-slice CT that uses the X-ray detection device 103 where detection elements are arranged in one column i.e., the one-dimensional direction (a channel direction only). In the multi-slice CT, an X-ray beam spreading in a conical or pyramid shape is irradiated from the X-ray generating device 102 that is the X-ray source according to the X-ray detection device 103. In the single-slice CT, an X-ray beam spreading like a fan is irradiated from the X-ray generating device 102. Normally, in scanning by the X-ray CT apparatus 1, an X-ray is irradiated while the gantry 100 is rotating around the object 3 placed on the bed (however, positioning scanning is excluded.).

A scanning mode where the bed is fixed during scanning and the X-ray generating device 102 rotates around the object 3 like a circle orbit is referred to as axial scanning. Also, a scanning mode where the bed moves continuously and the X-ray generating device 102 rotates around the object 3 like a spiral orbit is referred to as spiral scanning.

In case of the axial scanning, the bed device 101 keeps the bed resting during scanning. Also, in case of the spiral scanning, the bed device 101 moves the bed parallel in the body-axis direction of the object 3 during scanning according to the bed sending speed that is one of scanning conditions.

Figure 3:
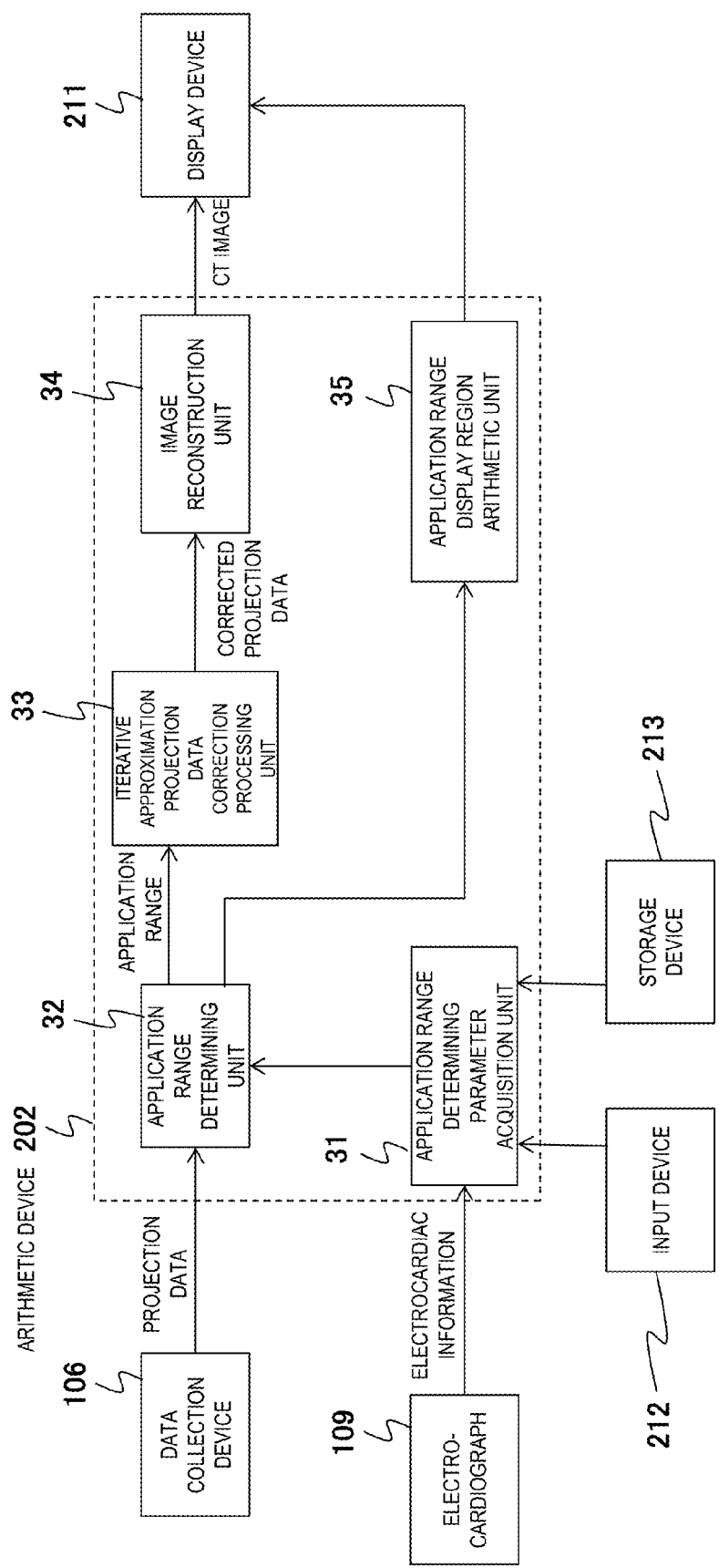
FIG. 3 is a functional block diagram of the calculation device 202.

Next, referring to FIG. 3, the functional configuration of the X-ray CT apparatus 1 of the present invention will be described. Particularly, FIG. 3 shows the functional configuration of the calculation device 202.

The calculation device 202 has the application range determining parameter acquisition unit 31, the application range determining unit 32, the iterative approximation projection data correction processing unit 33, the image reconstruction unit 34, and the application range display region calculation unit 35 as the main functional configuration.

Additionally, as the assumption of the present invention, the calculation device 202 uses a cost function of the formula (3) and an update formula of the formula (4) shown as follows to perform an iterative approximation projection data correction process for projection data.

The formulas (3) and (4) correspond to the cost function disclosed in the non-patent literature 1 (the formula (9) on p. 1274 in the non-patent literature 1) and the update formula (the formula (11) on the same page in the same patent literature) respectively.

$$\Phi(q) = \sum_{j \in T} \sum_{i \in X} d_{ij}(y_{ij} - p_{ij})^2 + \sum_{j \in T} \sum_{i \in X} \beta_{ij} \sum_{m \in N_i} w_{ijm}(p_{ij} - p_{mj})^2 \quad (3)$$

$$p_{ij}^{(n+1)} = \frac{y_{ij} + \frac{\beta_{ij}}{d_{ij}}\left(\sum_{m \in N_i^1} w_{ijm} p_{mj}^{(n+1)} + \sum_{m \in N_i^2} w_{ijm} p_{mj}^{(n)}\right)}{1 + \frac{\beta_{ij}}{d_{ij}} \sum_{m \in N_i} w_{ijm}} \quad (4)$$

Here, "p" is an updated projection value, "y" is an original projection value, "β" is a smoothing coefficient, "d" is a detection characteristic value, "i" is an index for time, "j" is an index for a position (of a detection element), "n" is a repetition number, and "w" is a weight.

Before performing an iterative approximation projection data correction process, the calculation device 202 determines a range to apply the iterative approximation projection data correction process (hereinafter, referred to as an application range). An application range is determined according to the examination purpose, the scanning conditions, etc. the application range includes a position range of a detection element and a time range. As the range for a position of a detection element, there are an application range in a slice direction and an application range in a channel direction. Also, because the X-ray CT apparatus 1 obtains projection data from a plurality of angle directions while rotating around the object 3, the range for time is a range of the rotation direction (view angle) of the gantry 100, in other words.

The above application range is expressed as ranges of the indexes "i" and "j" of the addition unit in the update formula and the cost function (the above formulas (4) and (3)) to be used for an iterative approximation projection data correction process. As described above, "i" is an index for time and "j" is an index for a position (of a detection element). The calculation device 202 calculates application ranges (of the indexes "i" and "j") based on the scanning conditions, the examination purpose, etc. to apply an iterative approximation projection data correction process to projection data in the application ranges.

The respective functional units shown in FIG. 3 will be described.

The application range determining parameter acquisition unit 31 acquires a parameter (hereinafter, referred to as an application range determining parameter) for determining an application range for an iterative approximation projection data correction process.

An application range determining parameter, for example, may be scanning condition information set for the X-ray CT apparatus 1, irradiation dose information, or image reconstruction condition information. Also, the parameter may be periodic movement information of organs, such as electrocardiographic information in electrocardiographic synchronous scanning. Also, the parameter may be information obtained by analyzing an image, such as a variation of a contrast monitoring image in contrast-agent imaging.

An application range determining parameter can be acquired from the external devices such as the input device 212, the storage device 213, and the electrocardiograph 109 and the storage regions (such as a RAM) in the calculation device 202.

For example, scanning condition information is various parameters such as an X-ray beam width and a body-axis direction scanning range.

The scanning condition information is input from the input device 212 by an operator before scanning. Alternatively, the scanning condition information is stored in the storage region in the storage device 213 and the calculation device 202.

A tube current and a tube voltage are included in irradiation dose information. An optimal value of irradiation dose information is calculated by the calculation device 202 based on scanning conditions, reconstruction conditions, a physique of an object, etc. and stored in the storage region in the calculation device 202. Alternatively, the value is stored in the storage device 213.

Image reconstruction condition information such as an ROI, an FOV, and a body-axis direction range to be reconstructed is input from the input device 212. Alternatively, the information is stored in the storage device 213.

Electrocardiographic information is acquired from the electrocardiograph 109 (see FIG. 3) is attached to the object 3 in real time during scanning the cardiac region etc.

A variation of a contrast monitoring image in scanning using a contrast-agent can be obtained from analysis results by the calculation device 202.

The application range determining unit 32 acquires projection data to be input from the data collection device 106.

Also, an application range determining parameter is acquired from the application range determining parameter acquisition unit 31.

Then, the application range determining unit 32 determines an application range for an iterative approximation projection data correction process to the acquired projection data. The application range is a range for improving the image quality. The purpose of the image quality improvement is roughly classified into two. One is a case where ideal image quality cannot be obtained due to scanning at a low exposure dose for the exposure dose reduction. The other is to further improve image quality of a target site with a sufficient exposure dose.

The application range determining unit 32 determines an application range for an iterative approximation projection data correction process based on an application range determining parameter such as scanning conditions. The application range determining unit 32 restricts a position range of a detection element to which correction processing is applied and a time range from among the entire projection data. The position range of a detection element means a channel direction range and a slice direction range of the detection element. Also, the time range means a range of a rotation angle (view angle) of the detection device.

The position range of the detection element corresponds to a range of the index "j" of the addition unit included in the above cost function (the formula (3)) and update formula (the formula (4)). Also, the time range corresponds to a range of the index "i" of the addition unit included in the above cost function (the formula (3)) and update formula (the formula (4)). The application range determining unit 32 outputs the determined application range to the iterative approximation projection data correction processing unit 33 and the application range display region calculation unit 35.

The details of the application range determination method using the respective application range determining parameters will be described in the respective embodiments.

The application range determining unit 32 determines a magnitude of smoothing coefficient included in the formula (4) according to the target image quality and the examination purpose. The smoothing coefficient is a coefficient showing a correction intensity.

The iterative approximation projection data correction processing unit 33 performs an iterative approximation projection data correction process for an application range determined by the application range determining unit 32. In the iterative approximation projection data correction process, the calculation device 202 applies the update formula of the formula (4) to projection data in the application range. Until the cost function shown in the formula (3) provides a desirable result, the calculation is repeated. After the calculation, the obtained projection value is output as correction projection data to the image reconstruction unit 34.

The image reconstruction unit 34 reconstructs CT images based on correction projection data input from the iterative approximation projection data correction processing unit 33. The image reconstruction unit 34 outputs the reconstructed CT images to the display device 211.

The application range display region calculation unit 35 performs calculation to display an application range determined by the application range determining unit 32. For example, an application range position on a CT image is calculated.

The display device 211 displays a CT image reconstructed by the image reconstruction unit 34 in addition to an application range of an iterative approximation projection data correction process. For example, the display device 211 clearly indicates the above application range on the CT image. It may be configured so that the boundary line between the inside and the outside of the application range is displayed. Additionally, a mode to display the boundary is not limited to a line, and the boundary may be displayed in another mode.

Next, referring to FIG. 4, the overall process flow of the X-ray CT apparatus 1 of the present invention will be described.

First, the X-ray CT apparatus 1 performs positioning scanning for the object 3. Next, the X-ray CT apparatus 1 performs various condition settings such as scanning conditions and reconstruction conditions based on the positioning image generated by positioning scanning. Then, the X-ray CT apparatus 1 performs tomographic scanning (main scanning) to acquire projection data (Step S101).

The calculation device 202 performs an iterative approximation projection data correction process for projection data to be acquired (Step S102). In the present invention, as described above, an application range of the iterative approximation projection data correction process is determined before executing repeated calculation for the iterative approximation projection data correction process. The determining method for an application range of the iterative approximation projection data correction process will be described in each embodiment. The calculation device 202 executes the iterative approximation projection data correction process only for projection data in an application range.

The calculation device 202 performs image reconstruction using correction projection data corrected by an iterative approximation projection data correction process to generate a CT image (Step S103). The calculation device 202 performs image reconstruction by the iterative approximation method, for example. Because a part of an application range of the projection data is corrected by the iterative approximation projection data correction process in the present invention, noise reduction is performed for a part of the correction projection data. Therefore, image quality in a site corresponding to the above application range is improved on a CT image generated by the correction projection data.

The calculation device 202 displays a CT image to be generated (noise-reduced image) on the display device 211. Also, the calculation device 202 may display a range to which an iterative approximation projection data correction process is applied on a CT image, for example (Step S104). The details of the display mode will be described later.

First Embodiment

Next, referring to FIGS. 5 to 12, the first embodiment will be described.

As described above, when an application range for an iterative approximation projection data correction process is restricted, streak artifacts may occur in the boundary region between the area in which correction processing was performed and the area in which correction processing was not performed. Therefore, in the first embodiment, the calculation device 202 set margin regions for the application range. Also, it is configured so that a smoothing coefficient included in the update formula of the iterative approximation projection data correction process continues smoothly near the boundaries between the inside and the outside of the application range. Specifically, the smoothing coefficient to be applied in margin regions is changed continuously so that the coefficient become smaller gradually from the application range toward the outside of the application range.

Figure 5:
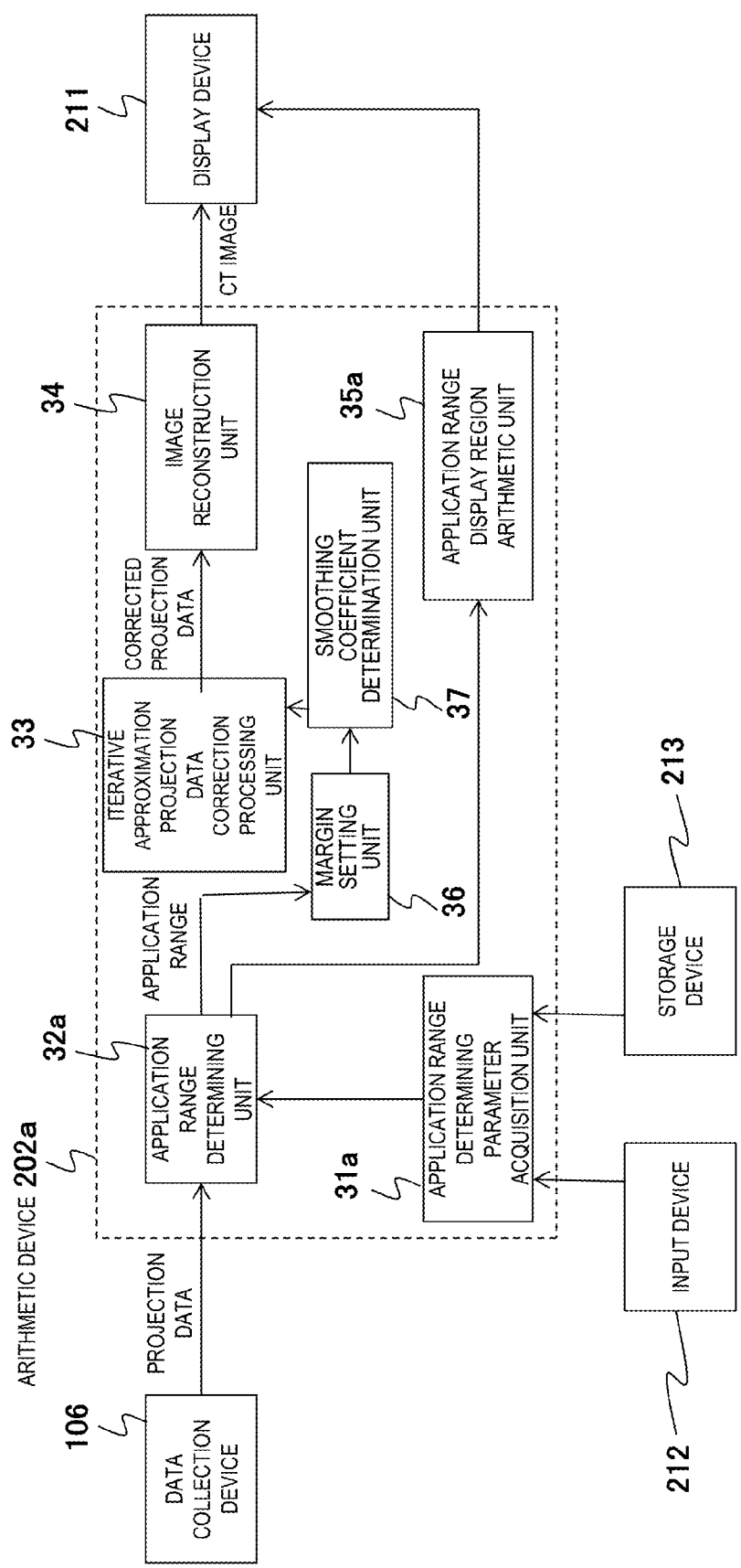
FIG. 5 is a functional block diagram of the calculation device 202a in the first embodiment.

FIG. 5 is a diagram showing the functional configuration of the calculation device 202a of the first embodiment.

Figure 4:
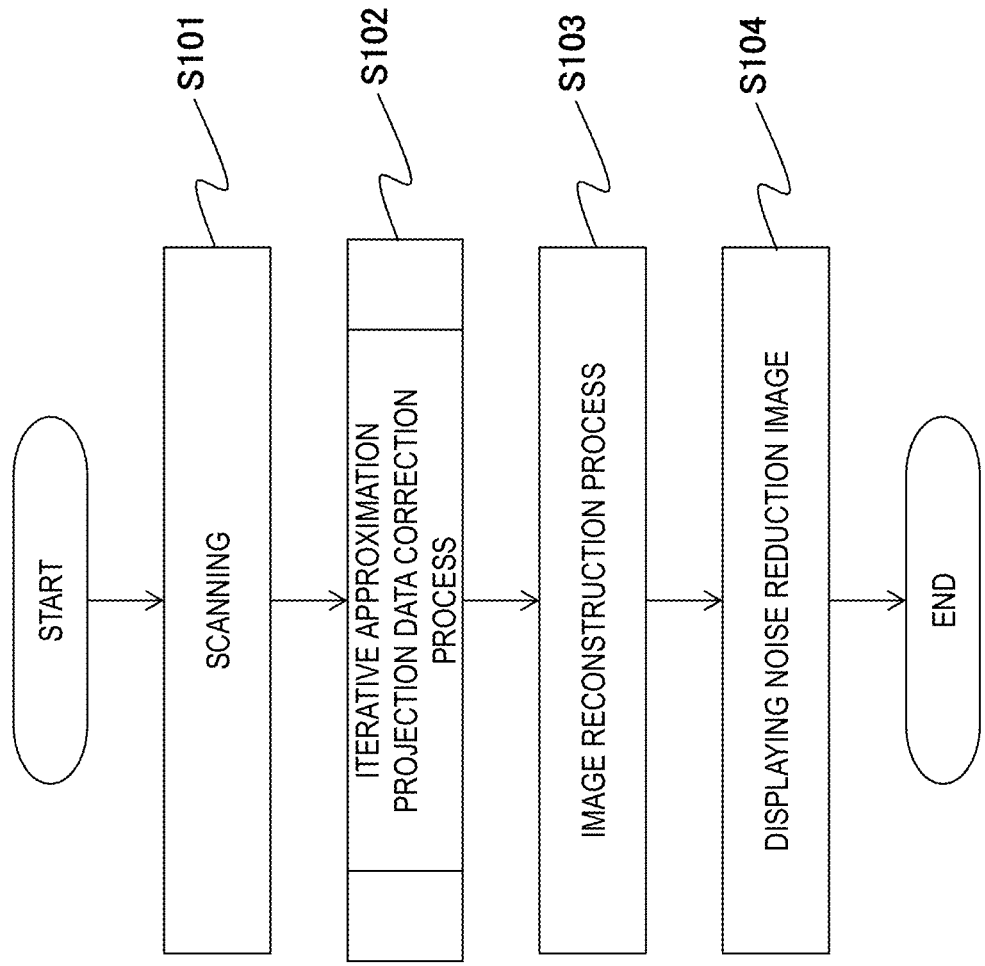
FIG. 4 is a flow chart showing the overall process flow.

The calculation device 202a of the first embodiment includes the margin setting unit 36 and the smoothing coefficient determination unit 37 in addition to the functional configuration of the calculation device 202 shown in FIG. 4. That is, the calculation device 202a of the first embodiment has the application range determining parameter acquisition unit 31a, the application range determining unit 32a, the margin setting unit 36, the smoothing coefficient determination unit 37, the iterative approximation projection data correction processing unit 33, the image reconstruction unit 34, and the application range display region calculation unit 35a.

Figure 2:
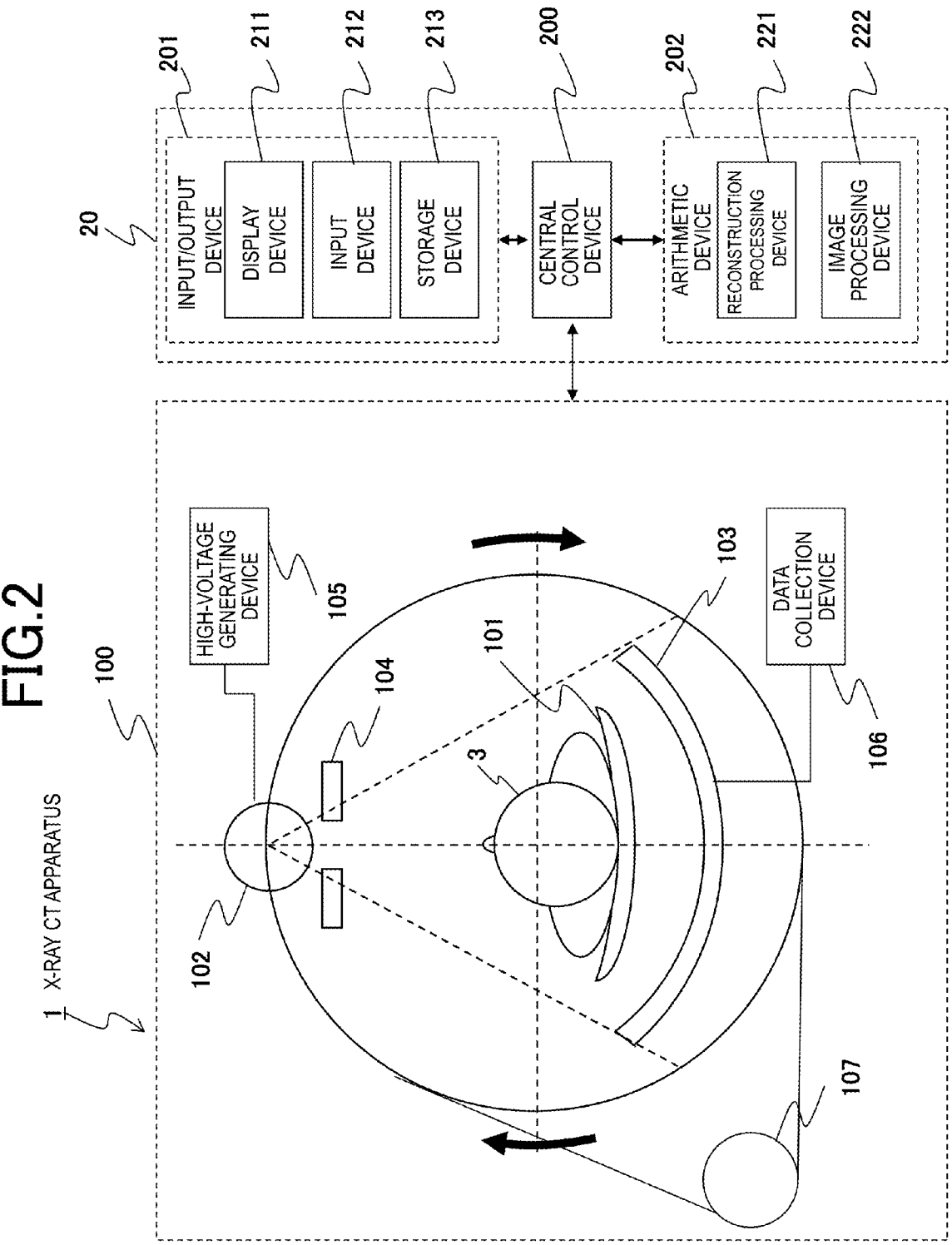
FIG. 2 is a hardware block diagram of the X-ray CT apparatus 1.

Additionally, the same symbols are used for the configuration elements similar to those shown in FIGS. 1, 2, and 3, and the repeated explanations are omitted. Also, although the calculation device 202a of the first embodiment is hardware similar to the calculation device 202 shown in FIG. 2, the symbols are different from the calculation device 202 shown in FIG. 2 due to the different functional configuration.

The application range determining parameter acquisition unit 31a of the first embodiment acquires an FOV of an X-ray beam width and a scanning range size in a cross-section as an application range determining parameter. The X-ray beam width is included in scanning condition information. The FOV is included in reconstruction condition information. The scanning condition information and reconstruction condition information may be the contents set in the input device 212 by an operator or the contents preset (stored in the storage device 213) for each examination purpose.

Figure 6:
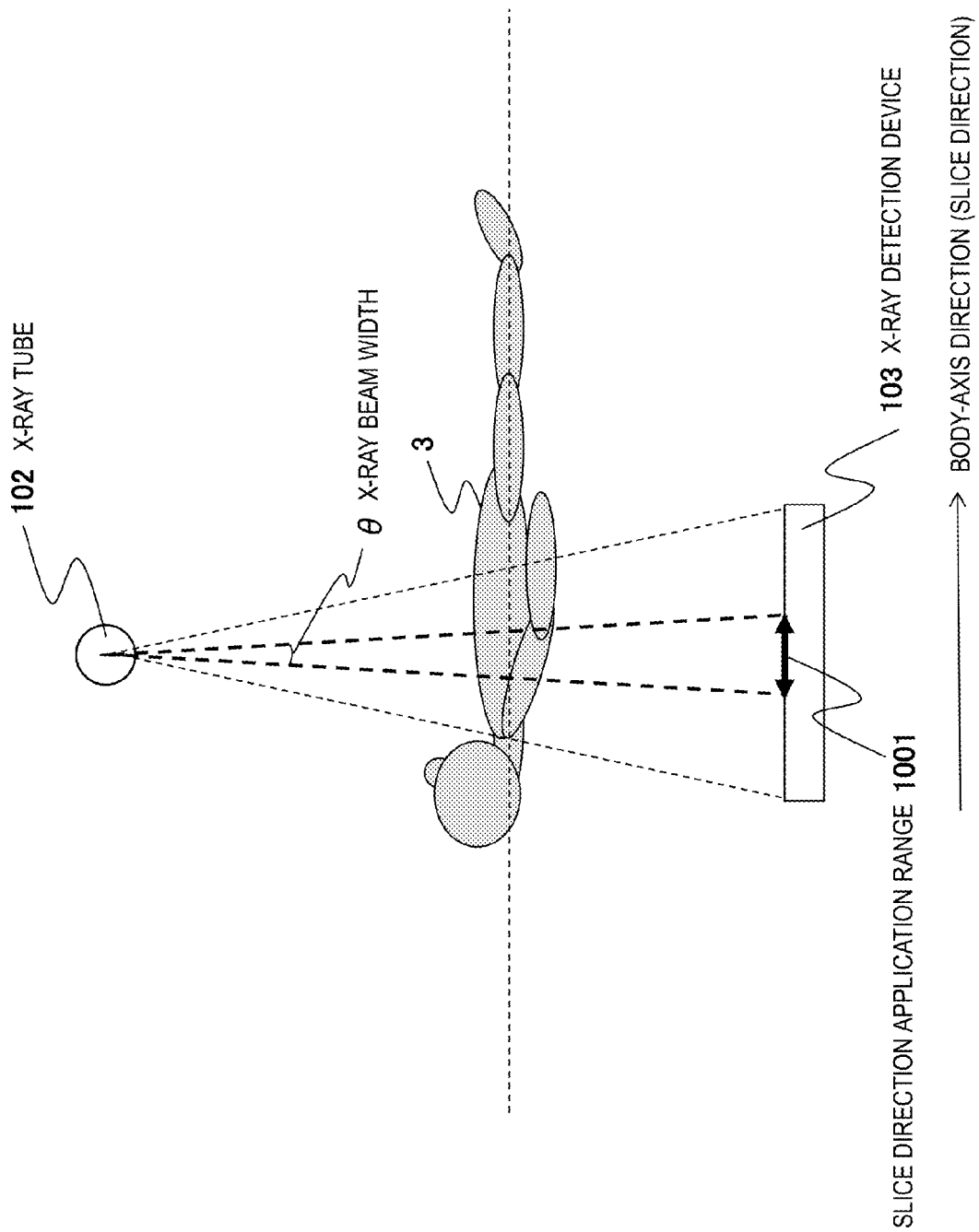
FIG. 6 is a diagram showing an example of the slice direction application range 1001.

The application range determining unit 32a determines an application range for an iterative approximation projection data correction process based on the X-ray beam width $\theta$. Specifically, a detection element range in the body-axis direction (slice direction) corresponding to the X-ray beam width $\theta$ is calculated, and then the calculated detection element range is specified as the slice direction application range 1001 of correction processing. FIG. 6 is a diagram viewing the body-axis direction of the object 3 in the horizontal direction of the diagram. As shown in FIG. 6, the flare angle $\theta$ in the body-axis direction of an X-ray beam irradiated from the X-ray tube 102 is an X-ray beam width. The application range determining unit 32a sets a detection element range in a slice direction corresponding to the X-ray beam width $\theta$ as the slice direction application range 1001 of correction processing.

Figure 7:
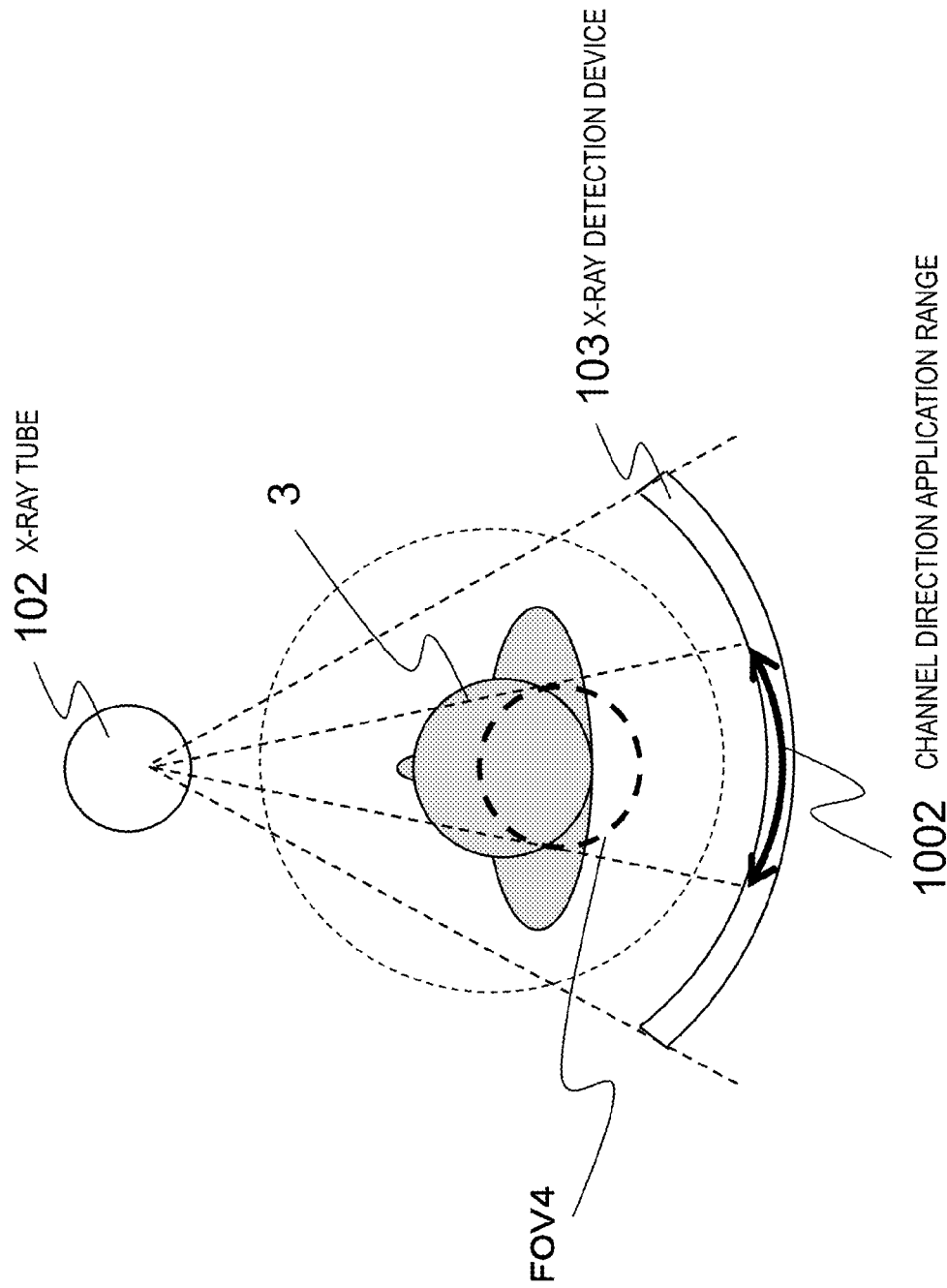
FIG. 7 is a diagram showing an example of the channel direction application range 1002.

Also, the application range determining unit 32a determines an application range for an iterative approximation projection data correction process based on an FOV. Specifically, the application range determining unit 32a calculates a detection element range in a channel direction corresponding to the FOV. Then, the calculated detection element range is set as the channel direction application range 1002 of correction processing. FIG. 7 is a diagram viewing the body-width (X) direction of the object 3 in the horizontal direction of the diagram and the body-axis direction in the depth direction of the diagram. The range 4 shown in the dot-dash line in FIG. 7 is set as the FOV. The application range determining unit 32a sets a detection element range in the channel direction corresponding to the FOV as the channel direction application range 1002 of correction processing.

The margin setting unit 36 of FIG. 5 sets margin regions for an application range determined by the application range determining unit 32a.

The update formula to be used for an iterative approximation projection data correction process includes weighting addition processing between adjacent elements as shown in the above formula (4). The margin setting unit 36 sets margins of calculation processing for based on an adjacent element range for performing the weighting addition processing. For example, if the adjacent element range for the weighting addition processing has two elements, one element margins for calculation processing are set on the both sides. Additionally, this is an example, and two or more element margins for calculation processing may be set.

Also, the margin setting unit 36 extends the application range determined by the application range determining unit 32a in order to prevent streak artifacts from occurring as described above. In this case, the margins are referred to as an application range margin. Sizes of the application range margins are desirably set in light of the range of influence in processes after an iterative approximation projection data correction process. For example, when filtering processing is performed after the iterative approximation projection data correction process, the margin setting unit 36 sets application range margins of the number of elements influencing on the filtering processing. Also, the direction of the application range margins is set according to the application range direction. For example, from among a channel direction and a slice direction, the application range margins are provided for at least either of the directions or both of the directions.

Figure 8:
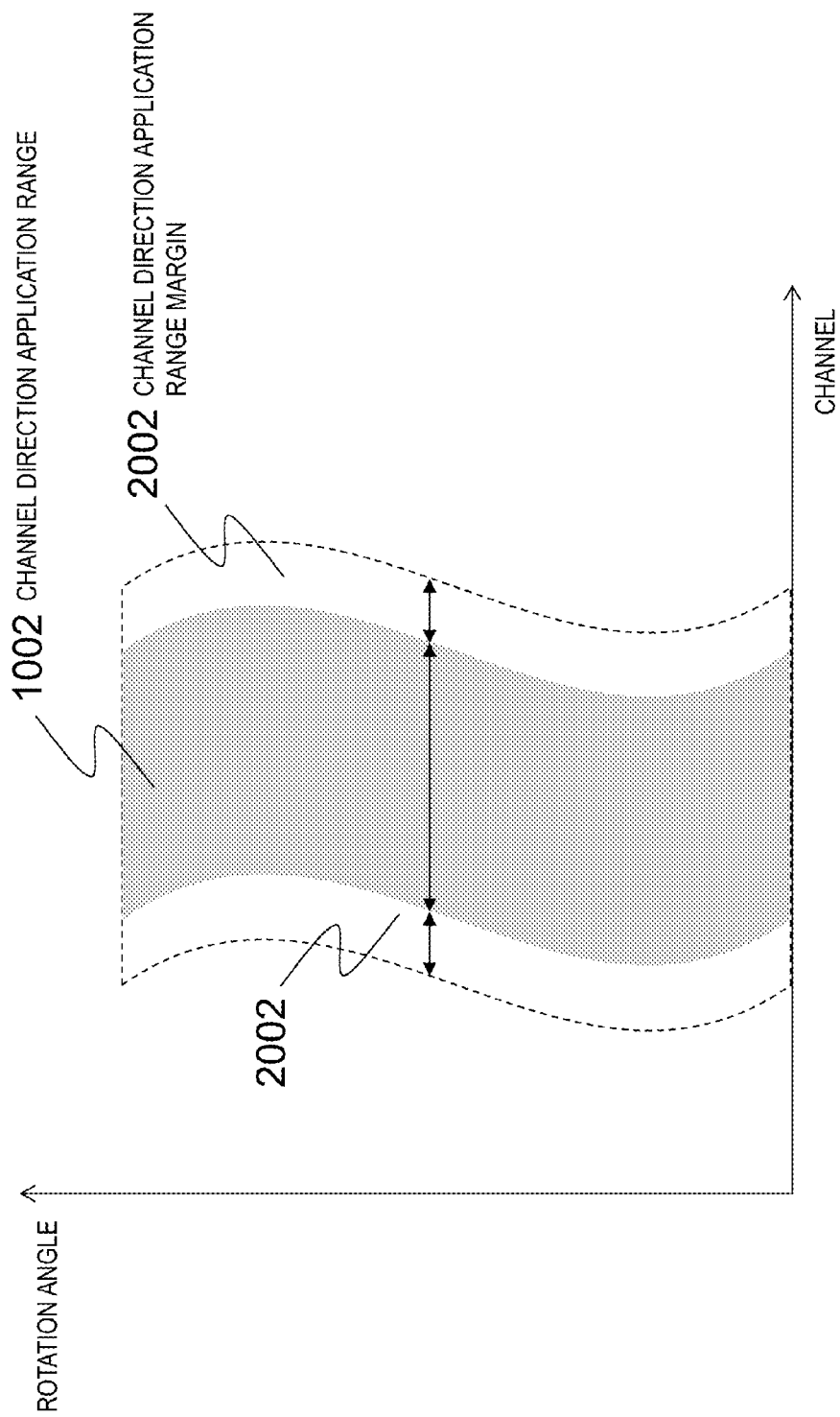
FIG. 8 is an example of the channel direction application range 1002 and the application range margin 2002 to be expressed on the sinogram 1000.

FIG. 8 is the sinogram 1000 of projection data of one cross section. The horizontal axis shows a channel position of a detection element, and the vertical axis shows a rotation angle. The sinogram 1000 shows a projection value of each detection element in each rotation angle position in gray-scale (shading).

For example, when the channel direction application range 1002 shown in FIG. 7 is expressed on the sinogram 1000, the range is that shown in gray in FIG. 8. The margin setting unit 36 sets the channel direction application range margins 2002 on the both sides of the channel direction of the channel direction application range 1002.

The smoothing coefficient determination unit 37 in FIG. 5 calculates a smoothing coefficient to be applied to an application range and application range margins. The smoothing coefficient determination unit 37 sets a smoothing coefficient to be applied to the application range margins so that it becomes continuously smaller from the application range toward the outside of the application range. Thus, the smoothing coefficient is smoothly changed in the boundaries (application range margins) between the inside and the outside of the application range, which can reduce streak artifacts. The smoothing coefficient determination unit 37 changes a smoothing coefficient smoothly in the boundaries between the inside and the outside of the application range for both of the channel direction and the body-axis direction.

Figure 9:
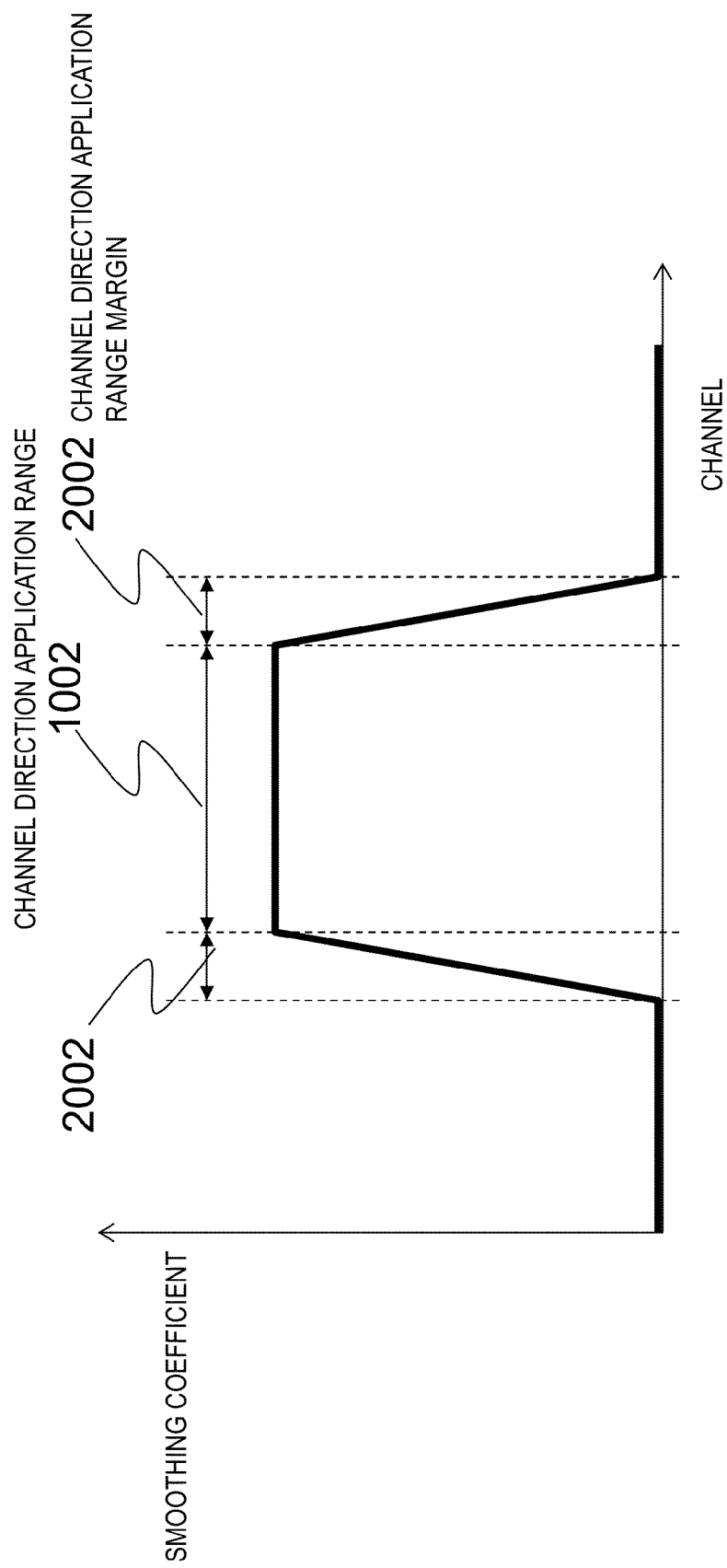
FIG. 9 is a diagram explaining the relationship between a channel direction application range, an application range margin, and a smoothing coefficient change.

FIG. 9 is a diagram showing a change of a smoothing coefficient near the boundaries between the inside and the outside of the application range in the channel direction. As shown in FIG. 9, the application range margins 2002 are set on the boundaries between the channel direction application range 1002 and the outside of the application range. The smoothing coefficient determination unit 37 sets a smoothing coefficient to be applied to the inside of the application range 1002 to a constant value. Then, a smoothing coefficient to be applied to the outside region of the application range 1002 is set to "0". Additionally, in the boundary region between the inside and the outside of the application range (the application range margins 2002), a smoothing coefficient is set so that it is changed smoothly.

Figure 10:
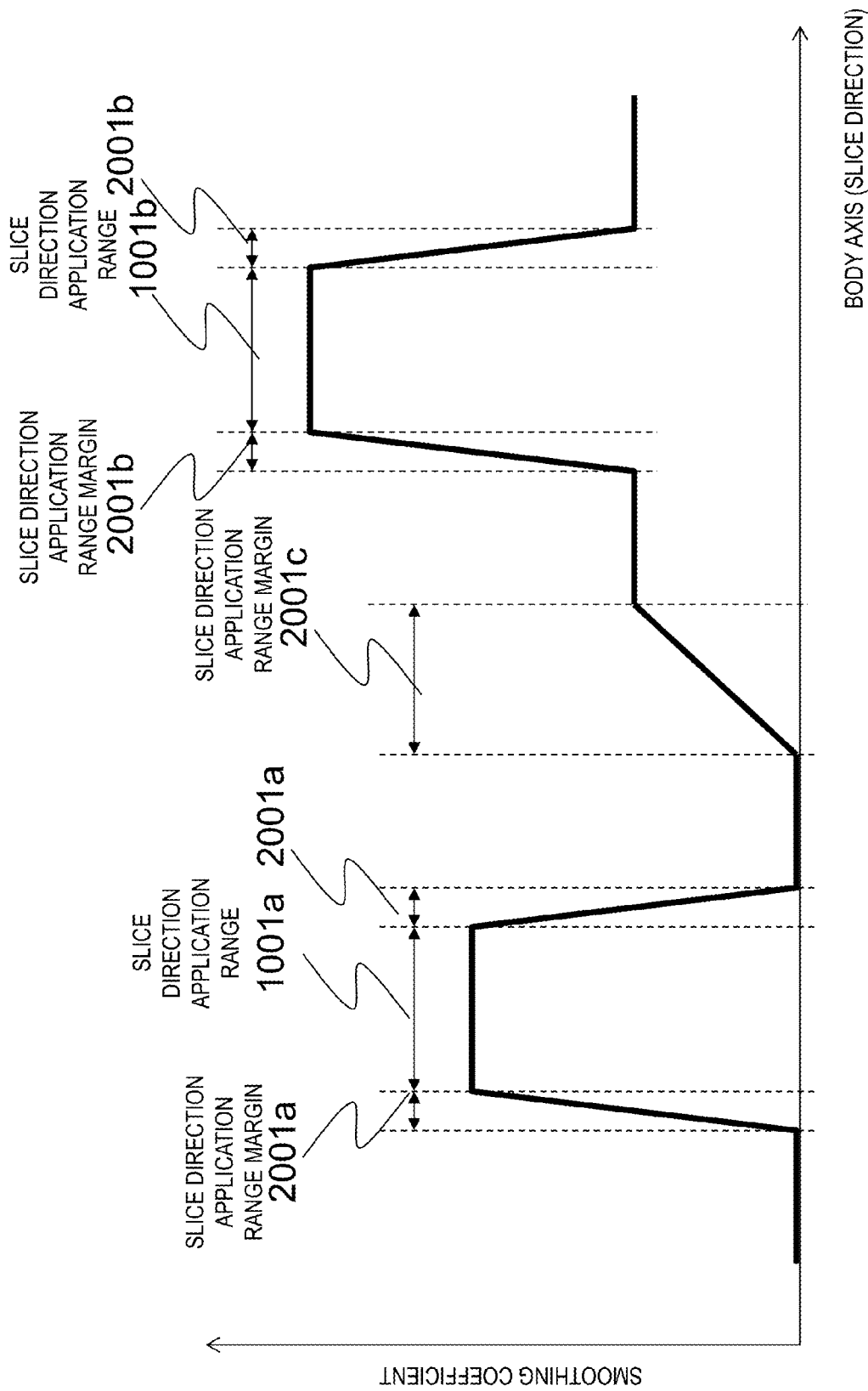
FIG. 10 is a diagram explaining the relationship between a slice direction application range as well as an application range margin and a smoothing coefficient change.

Similarly, also in the slice direction, the margin setting unit 36 sets the slice direction application range margins 2001 (2001a, 2001b, and 2001c) for the slice direction application range 1001 (1001a and 1001b) (see FIG. 10). Also, the smoothing coefficient determination unit 37 sets a smoothing coefficient also for the slice direction similarly to the channel direction.

FIG. 10 is a diagram showing a change of a smoothing coefficient in the slice direction. In the example of FIG. 10, the slice direction application ranges 1001a and 1001b are set for a plurality of regions in the body-axis direction. As shown in FIG. 10, the application range margins 2001a and 2001b are set respectively for the boundary between the application ranges 1001a and 1001b and the outside region of the application ranges. The smoothing coefficient determination unit 37 may set different smoothing coefficients for the respective application ranges 1001a and 1001b as shown in FIG. 10. In case of setting different smoothing coefficients for the respective application ranges 1001a and 1001b, as shown in FIG. 10, the smoothing coefficient may be changed in stages by setting the application range margin 2001c widely in the intermediate region between the application ranges 1001a and 1001b.

The application range display region calculation unit 35a in FIG. 5 calculates a position on the CT image of the application range determined by the application range determining unit 32. In the first embodiment, application range margins are provided around an application range. Therefore, it is desirable that both positions on a CT image of the application range and the application range margins are calculated. Additionally, it may be configured so that an operator switches whether to display the boundaries between the application range and the application range margins by a selection operation or not.

Figure 11:
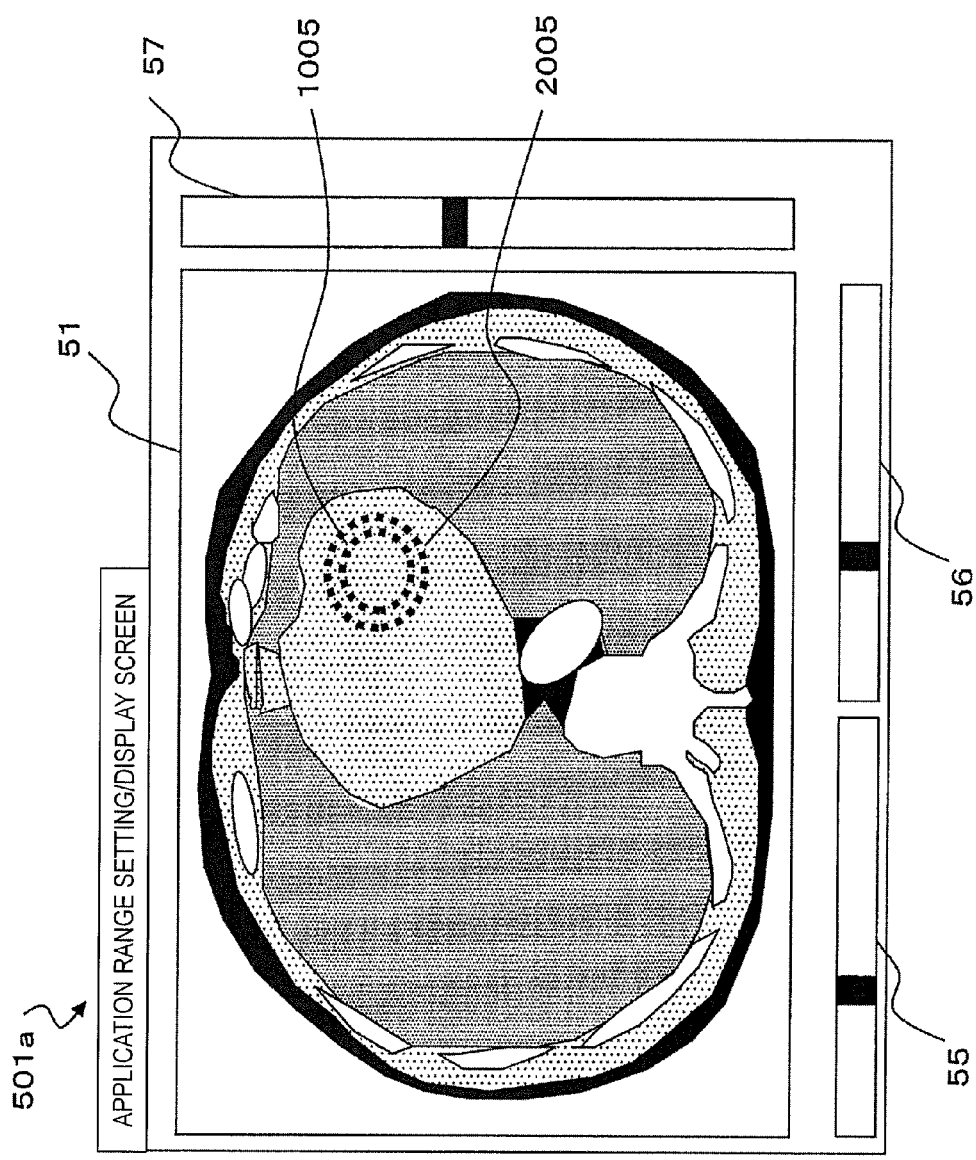
FIG. 11 is a diagram showing an example of the application range setting/display screen 501a in the first embodiment.

FIG. 11 is a diagram showing an example of the application range setting/display screen 501a. In the example of FIG. 11, the boundary line 1005 showing a application range and the boundary line 2005 showing a application range margin are displayed on a CT image displayed in the CT image display area 51. Either one of the boundary line 1005 showing the application range and the boundary line 2005 showing the application range margin may be displayed. Also, it may be configured so that an operator can switch whether to display the boundary lines 1005 and 2005.

Also, on the application range setting/display screen 501a shown in FIG. 11, an input operation unit (the slide bars 55, 56, and 57) for moving the respective boundary lines 1005 and 2005 or changing the sizes may be provided. Intuitive operation can be achieved by using a GUI adjusting the sizes and positions of the boundary lines 1005 and 2005 as the input operation unit, for example. When an operator operates the input operation unit to move the positions of the boundary lines 1005 and 2005 and change the sizes, the application range determining unit 32a and the margin setting unit 36 resets the application range or the application range margin for an iterative approximation projection data correction process to the moved positions or changed sizes. The iterative approximation projection data correction processing unit 33 performs the iterative approximation projection data correction process again for the reset application range etc.

Figure 12:
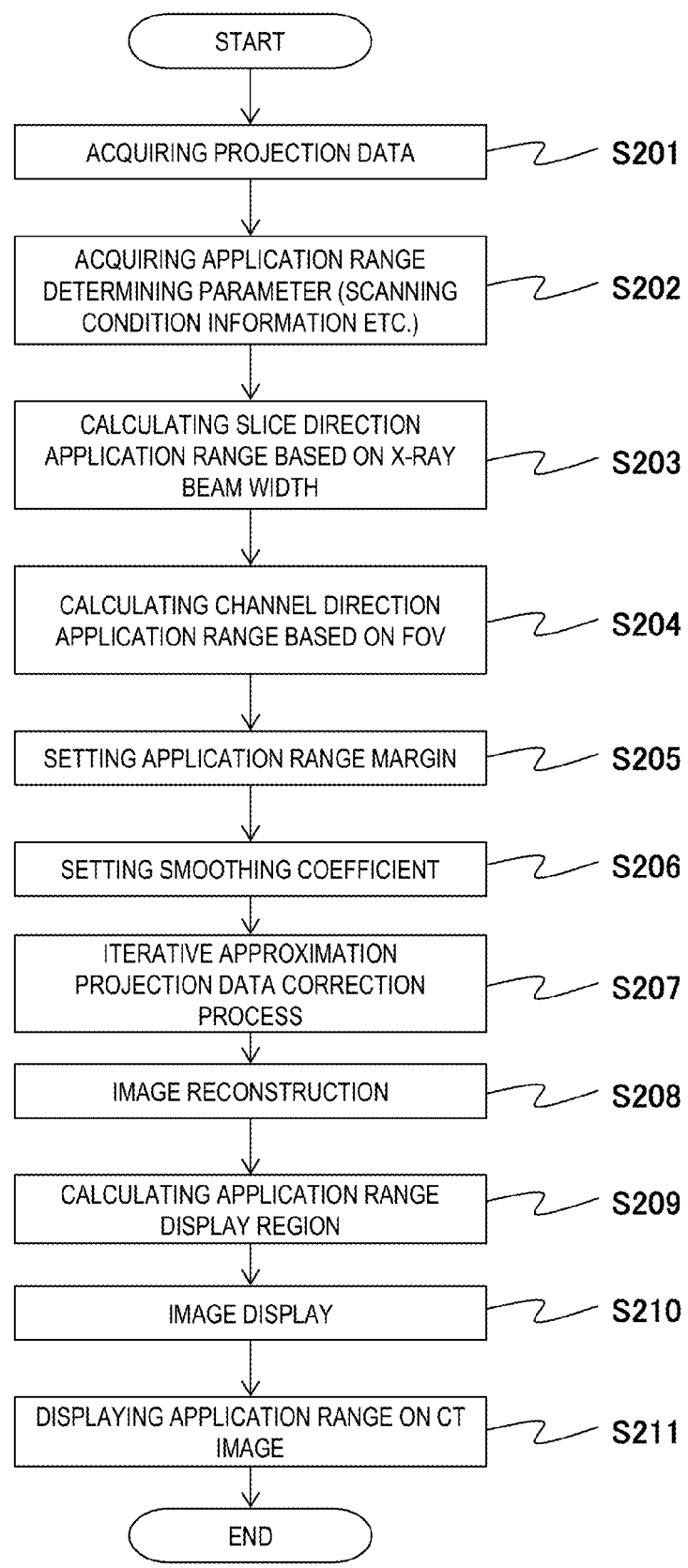
FIG. 12 is a flow chart showing the process flow in the first embodiment.

FIG. 12 is a flow chart describing the process flow executed by the calculation device 202a of the first embodiment.

The calculation device 202a acquires projection data from the data collection device 106 (Step S201). Also, the calculation device 202a (the application range determining unit 32a) acquires scanning condition information etc. (Step S202). The scanning condition information to be acquired is the X-ray beam width θ and an FOV.

The calculation device 202a calculates the slice direction application range 1001 based on an X-ray beam width as shown in FIG. 6 (Step S203). Then, the channel direction application range 1002 is calculated based on an FOV as shown in FIG. 7 (Step S204).

Because an amount of data to be deleted is large when restricting an application range in a slice direction, the slice direction application range 1001 is determined first.

Next, the calculation device 202a sets the application range margins 2001 and 2002 corresponding to each application range (Step S205).

The calculation device 202a calculates a smoothing coefficient to be applied to an application range and application range margins (Step S206). As shown in FIGS. 9 and 10, the smoothing coefficient is changed so that it continues smoothly inside and outside the application range.

Next, the calculation device 202a applies the smoothing coefficient calculated in Step S206 to the application range and the application range margins determined in the processes of Steps S203 to S205 in order to perform an iterative approximation projection data correction process (Step S207).

The application range determined in the processes of Steps S203 to S204 is expressed as the range of the index "j" for a position from among the indexes "i" and "j" included in the update formula (the above formula (4)) of an iterative approximation projection data correction process. Also, a smoothing coefficient corresponds to β included in the update formula.

The calculation device 202a outputs correction projection data as a result of an iterative approximation projection data correction process and sends it to the reconstruction processing device 221.

The reconstruction processing device 221 performs image reconstruction using correction projection data corrected by an iterative approximation projection data correction process and generates a CT image (Step S208). The reconstruction processing device 221, for example, performs image reconstruction by the iterative approximation method. Because a part of an application range of projection data was corrected by an iterative approximation projection data correction process in the present invention, noise-reduction is performed for a part of the correction projection data. Image quality at the site corresponding to the above application range is improved on the CT image to be generated by the correction projection data.

The calculation device 202a calculates a display region of an application range on a CT image (Step S209).

The calculation device 202a displays a generated CT image on the display device 211 (Step S210). At this time, the calculation device 202 displays a range where an iterative approximation projection data correction process was applied on the CT image as shown in FIG. 11 (Step S211).

As described above, the calculation device 202a of the first embodiment first restricts a range to apply an iterative approximation projection data correction process based on scanning conditions or reconstruction conditions such as an X-ray beam width and an FOV when performing an iterative approximation process of projection data. Also, application range margins are provided in regions adjacent to an application range, and a smoothing coefficient is set so that an intensity of correction processing becomes smooth in the boundary between the inside and the outside of the application range. Then, the above smoothing coefficient is applied to the application range and the application range margins to execute an iterative approximation projection data correction process.

Hence, because the iterative approximation projection data correction process can be limited to a part of projection data, the processing time can be reduced. Also, because an application range is set based on scanning conditions and reconstruction conditions, processing time can be reduced properly according to the purpose of CT examination. Also, because an application range is determined by scanning conditions, reconstruction conditions, etc., correction processing is performed for projection data corresponding to a target site. Therefore, low-noise images can be generated in a short time. Also, margins are provided around an application range, and a smoothing coefficient is set so that a correction intensity becomes smaller gradually according to the distance from the application range, which can reduce difference due to an image quality change of the inside and the outside of the application range. Also, because the boundary line between an application range and the outside of the application range is superimposed and displayed on a generated CT image, a region for which correction processing was performed can be visually recognized on the CT image during the observation.

Second Embodiment

Next, referring to FIGS. 13 to 18, the second embodiment will be described in detail.

In the second embodiment, the X-ray CT apparatus 1 uses irradiation dose information as a parameter to determine an application range of an iterative approximation projection data correction process. The irradiation dose information is parameters such as an X-ray tube current and a tube voltage. The irradiation dose information is determined based on scanning conditions, a scanning site, a physique of an object, etc. The calculation device 202 of the X-ray CT apparatus calculates a change curve of an optimal dose to be irradiated to each body-axis direction position in prior to scanning. Normally, a sufficient irradiation dose to meet target image quality is output at a diagnostic site (target site). On the other hand, by using a low irradiation dose required only for image reconstruction for the other sites, exposure dose reduction is enhanced.

In the second embodiment, by utilizing irradiation dose information to be used in scanning, an application range for an iterative approximation projection data correction process is determined.

Figure 13:
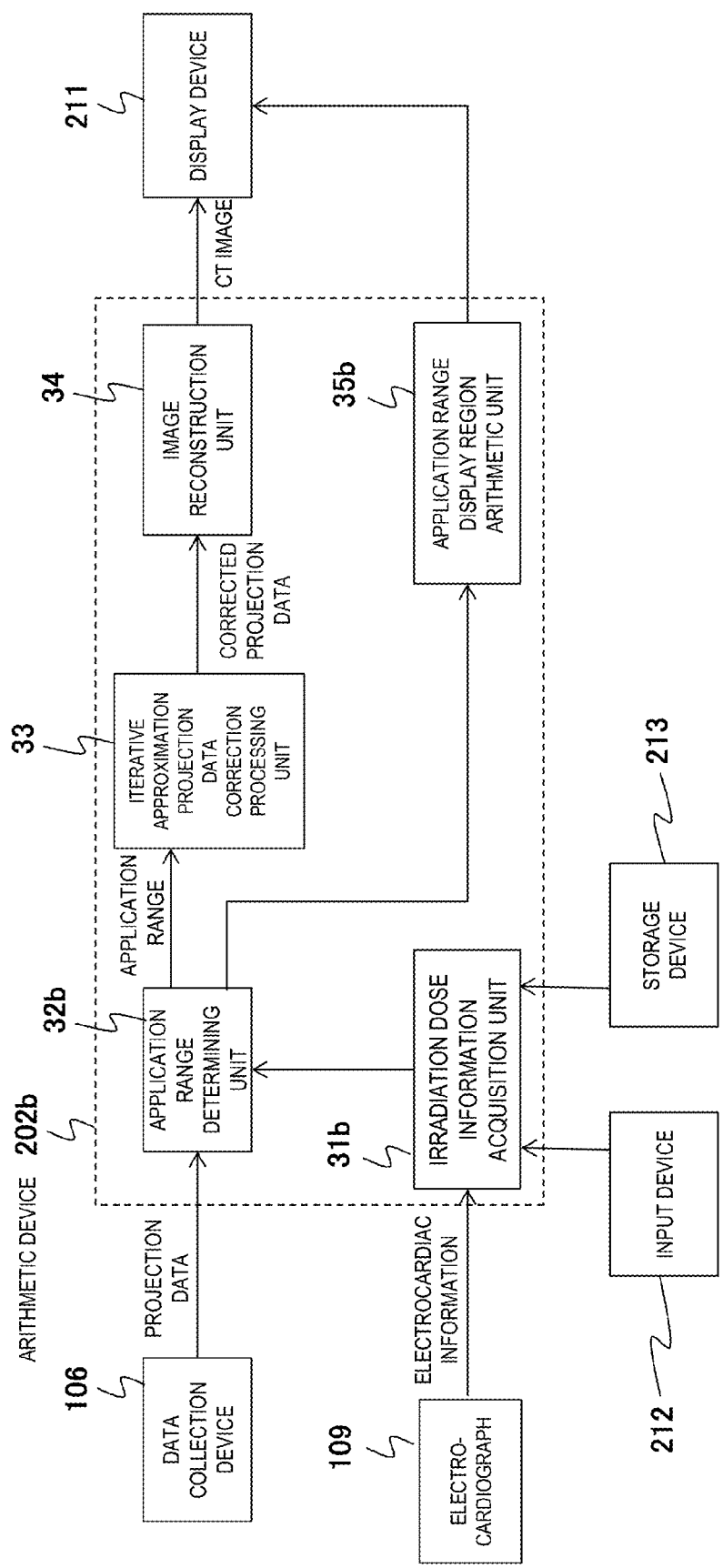
FIG. 13 is a functional block diagram of the calculation device 202b in the second embodiment.

FIG. 13 is a diagram showing the functional configuration of the calculation device 202b of the second embodiment.

In the second embodiment, the irradiation dose information acquisition unit 31b is provided instead of the application range determining parameter acquisition unit 31 of the calculation device 202 shown in FIG. 3.

As shown in FIG. 13, the calculation device 202b of the second embodiment has the irradiation dose information acquisition unit 31b, the application range determining unit 32b, the iterative approximation projection data correction processing unit 33, the image reconstruction unit 34, and the application range display region calculation unit 35.

Additionally, the same symbols are used for the configuration elements similar to those shown in FIGS. 1, 2, and 3, and the repeated explanations are omitted. Also, although the calculation device 202b of the second embodiment is hardware similar to the calculation device 202 shown in FIG. 2, the symbols are different from the calculation device 202 in FIG. 2 due to the different functional configuration.

Figure 14:
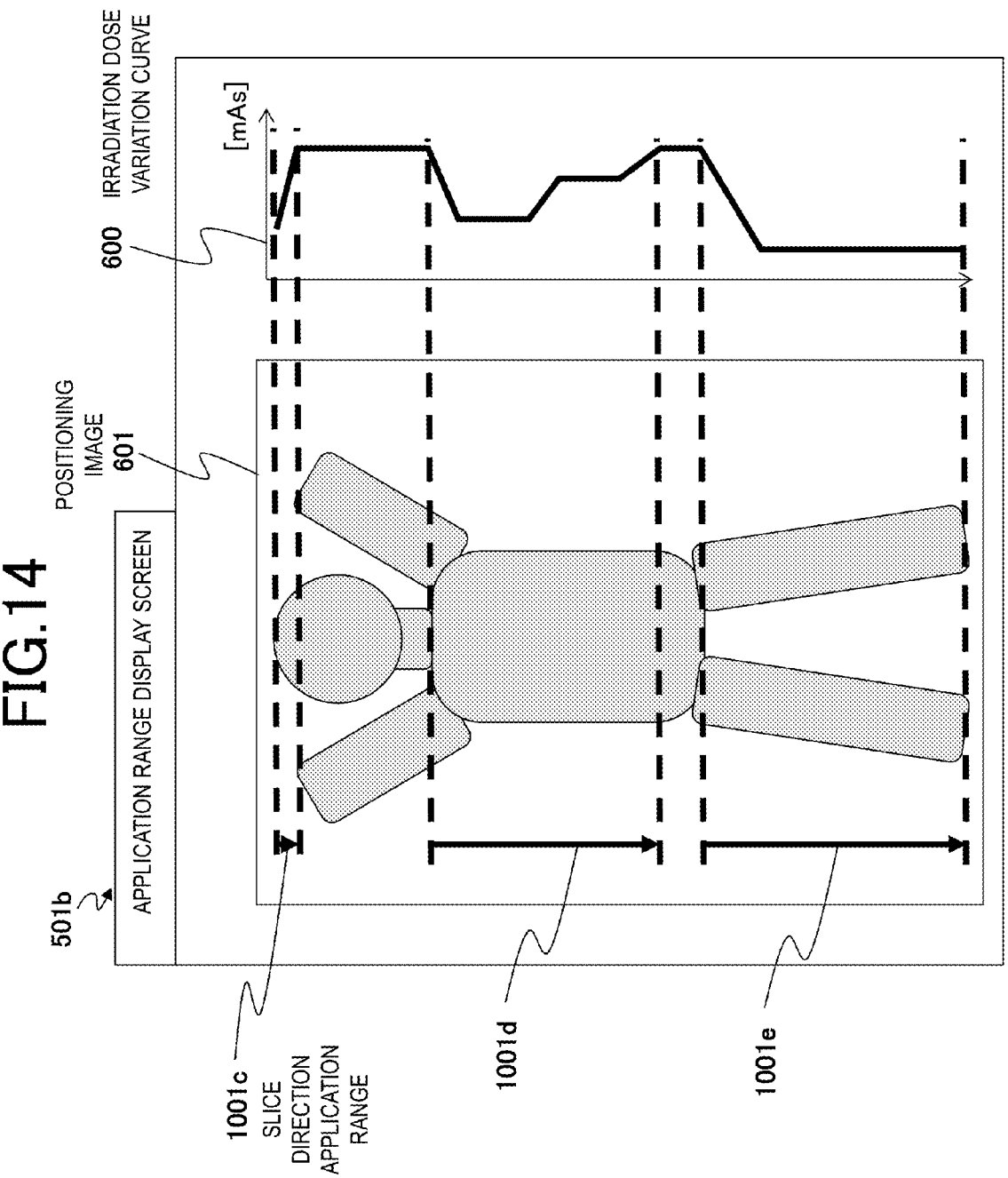
FIG. 14 is a diagram showing an example of the application range display screen 501b in the second embodiment.

FIG. 14 is an example of the application range display screen 501b of the second embodiment. The positioning image 601 and the irradiation dose variation curve 600 are displayed on the application range display screen 501b. Also, the body-axis direction position of the positioning image 601 corresponds to that of the irradiation dose variation curve 600.

The irradiation dose information acquisition unit 31b of the second embodiment acquires irradiation dose information as a parameter to determine an application range. The irradiation dose information is, for example, the irradiation dose variation curve 600 shown in FIG. 14. The irradiation dose variation curve 600 shows a change of an irradiation dose [mAs] according to the body-axis direction position. The irradiation dose information that is calculated by the calculation device 202b based on scanning conditions etc. or that is preset may be utilized. The irradiation dose information may also be generated based on electrocardiographic information to be input from the electrocardiograph 109 in electrocardiographic synchronous scanning etc.

In the present embodiment, as an example, description will be made for a case where the whole body (including the heart) is scanned while changing an irradiation dose. However, even in a case other than the whole-body scanning including the heart, the present invention can be applied.

The application range determining unit 32b calculates a range in the body-axis direction (slice direction) to which an iterative approximation projection data correction process is applied based on irradiation dose information input from the irradiation dose information acquisition unit 31b. For example, the application range determining unit 32b sets a threshold value for the irradiation dose variation curve 600.

Then, a body-axis direction range with an irradiation dose smaller than the threshold value is set as an application range. Alternatively, a body-axis direction range with an irradiation dose larger than the threshold value may also be set as an application range.

Setting a range with an irradiation dose smaller than a threshold value as an application range has a purpose to improve image quality by correcting projection data for a range scanned with a small irradiation dose.

On the other hand, setting a range with an irradiation dose larger than a threshold value as an application range has a purpose to further improve image quality of a diagnostic image by correcting projection data of a range including a target site.

The target site is normally scanned with a sufficiently large irradiation dose.

Also, the application range determining unit 32b may determine an application range based on whether there is a variation (a derivative value) in the body-axis direction of an irradiation dose.

For example, an irradiation dose that the irradiation dose variation curve 600 shows in FIG. 14 is changed significantly in the range of the calvaria and the range from the thorax to the abdomen of the object 3. The application range determining unit 32b sets the slice direction ranges with a large variation of an irradiation dose as the slice direction application ranges 1001c and 1001d of correction processing. Also, the lower extremities are scanned with a small irradiation dose. A slice direction range that is scanned with an irradiation dose lower than a predetermined threshold value is set as the slice direction application range 1001e of correction processing.

Additionally, the application range determining unit 32b calculates a range of a rotation direction to which an iterative approximation projection data correction process is applied based on a change of an irradiation dose in the rotation direction.

Figure 15:
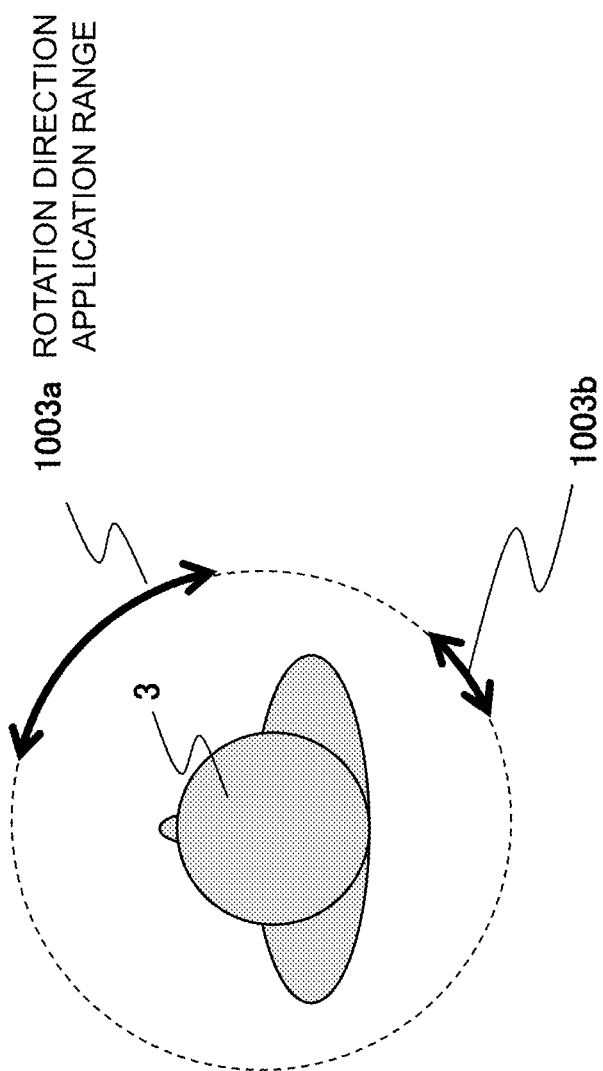
FIG. 15 is a diagram explaining the rotation direction application ranges 1003a and 1003b.

FIG. 15 is a diagram expressing the rotation direction application ranges 1003a and 1003b.

The application range determining unit 32b sets a threshold value for an irradiation dose changing depending on the rotation angle direction and restricts an application range of an iterative approximation projection data correction process to a rotation angle range larger or smaller than the threshold value. Alternatively, an application range may be restricted according to whether there is a variation (a derivative value) in the rotation angle direction of an irradiation dose.

Also, in cardiac scanning, the application range determining unit 32b may determine an application range on the basis of the waveform (such as the R wave) characteristic of an electrocardiogram.

Figure 16:
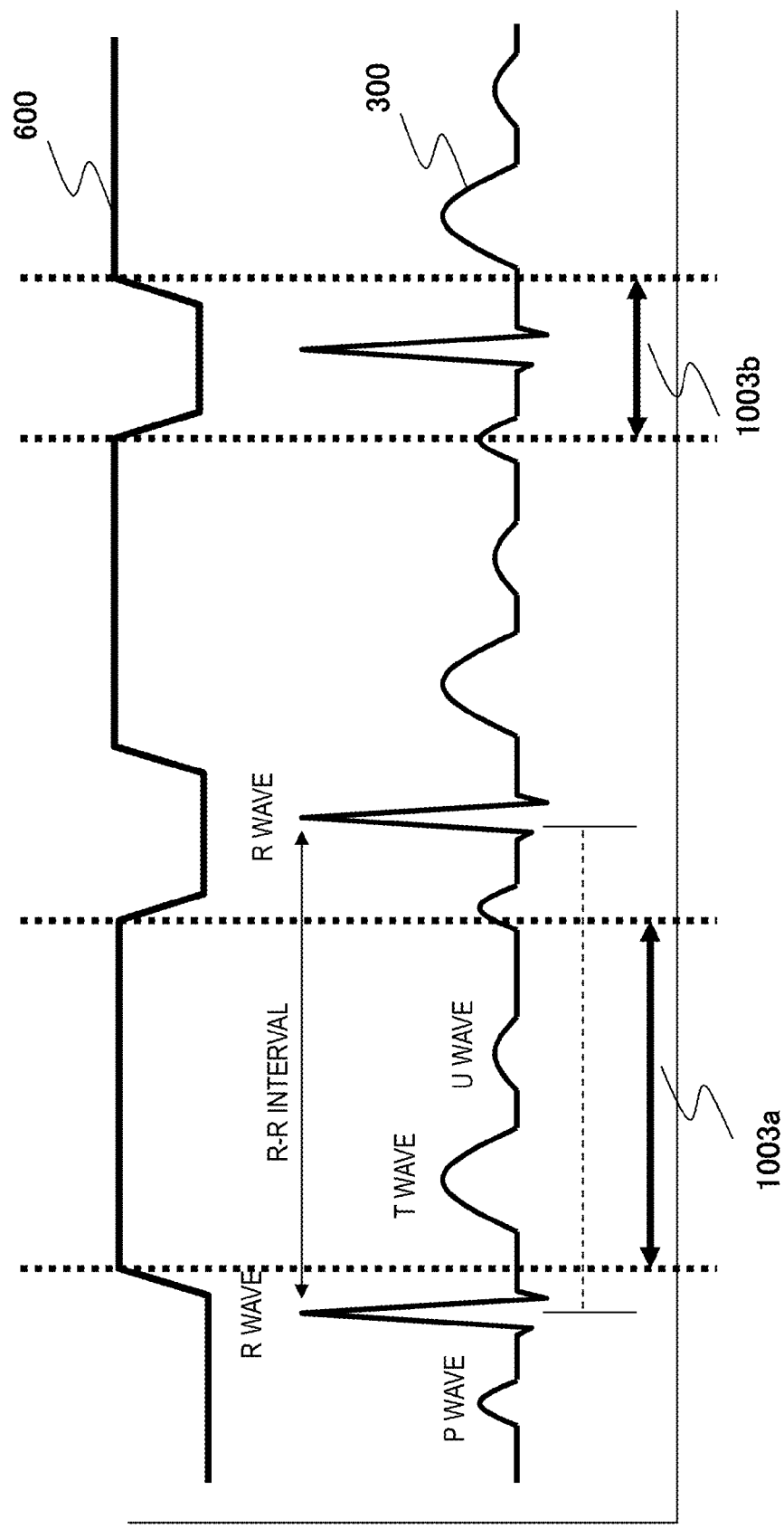
FIG. 16 is a diagram showing a relationship between the electrocardiographic information 300 and the irradiation dose variation curve 600.

FIG. 16 is a diagram showing an electrocardiographic waveform acquired in cardiac scanning and an irradiation dose determined according to the electrocardiographic waveform. The horizontal axis shows the time.

As shown in FIG. 16, in electrocardiographic synchronous scanning (ECG: Electrocardiogram), in order to reduce motion artifacts due to cardiac movement, a sufficient irradiation dose is irradiated in a range including a cardiac phase (static cardiac phase) optimal for scanning based on electrocardiographic information. An irradiation dose to be irradiated in the other phases is low.

The application range determining unit 32b sets a rotation direction range (time direction range) in which an irradiation dose is larger than a predetermined threshold value as the rotation direction application range 1003a of correction processing. Alternatively, a rotation direction range (time direction range) in which an irradiation dose is equal or less than a predetermined threshold value may be set as the rotation direction application range 1003b of correction processing.

The rotation direction application ranges 1003a and 1003b shown in FIG. 15 respectively corresponds to those in FIG. 16.

Figure 17:
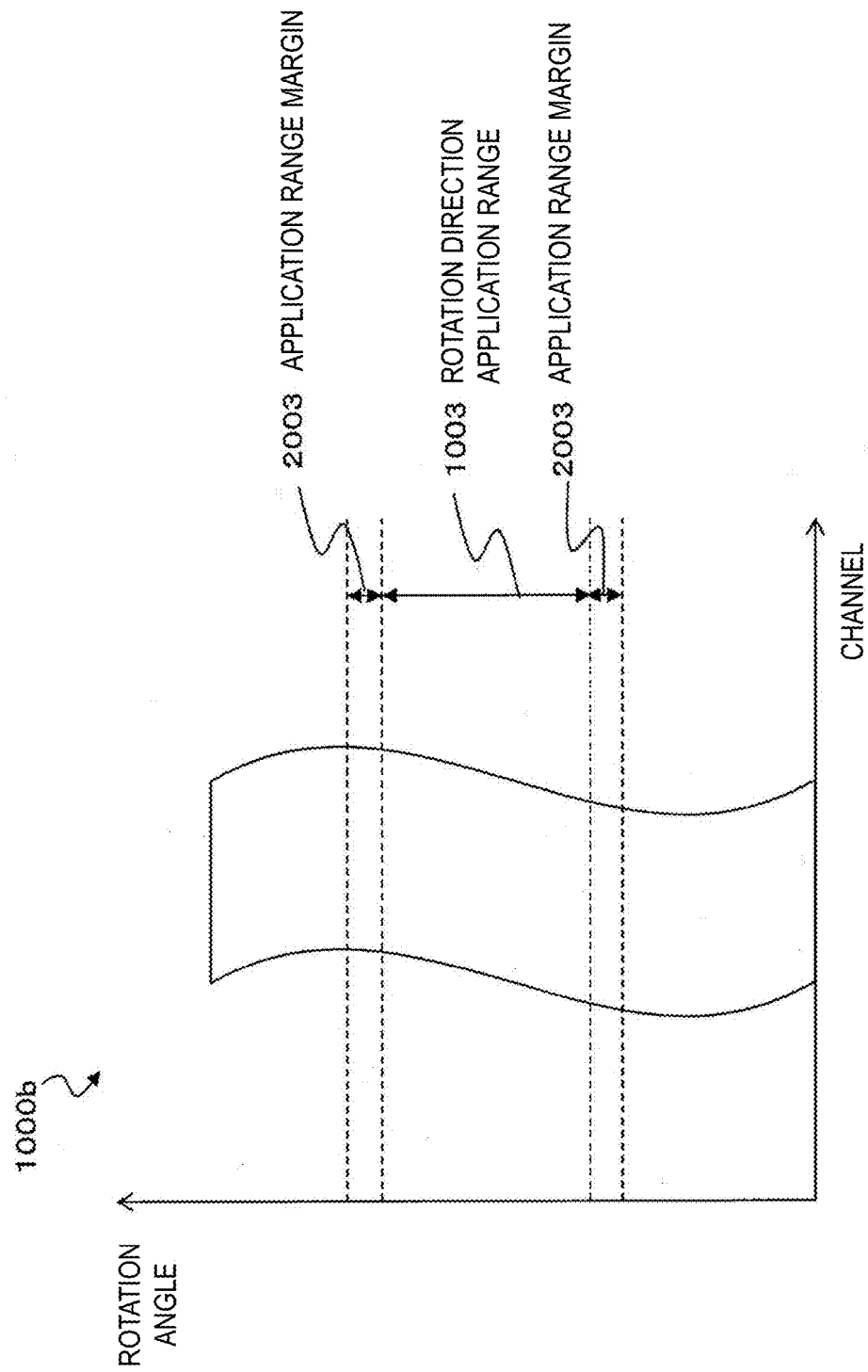
FIG. 17 is an example of the rotation direction application range 1003 and the application range margin 2003 to be expressed on the sinogram 1000b.

FIG. 17 is the sinogram 1000b of projection data. The horizontal axis shows a channel position of a detection element, and the vertical axis shows a rotation angle position.

The rotation direction application range 1003b on the sinogram 1000b is expressed as a range shown in the dotted lines and the arrows in FIG. 17, for example. A predetermined range in the rotation angle direction is restricted as the application range 1003. Additionally, as described in the first embodiment, the application range margin 2003 may be set also for the rotation angle direction.

The application range display region calculation unit 35b of the second embodiment calculates display data to display an application range determined by the application range determining unit 32b.

FIG. 14 is a diagram showing an example of the application range display screen 501b.

In the example of FIG. 14, the irradiation dose variation curve 600 is shown so as to correspond to the body-axis direction position of the positioning image 601. Also, the boundary lines, the arrows, etc. showing the slice direction application ranges 1001c, 1001d, and 1001e are displayed on the positioning image 601.

Additionally, as shown in FIG. 15, it may be configured so that the diagram showing the rotation direction application ranges 1003a and 1003b is displayed in the application range display screen 501b.

Also, when electrocardiographic synchronous scanning is being performed, it may be configured so that the boundary lines and the arrows showing the application ranges 1003a and 1003b are displayed on the electrocardiogram 300 and the irradiation dose variation curve 600 as shown in FIG. 16.

Also, in the application range display screen 501b of FIG. 14, an input operation unit to move the marks (the boundary lines and the arrows in FIGS. 14, 15, and 16) showing application ranges to be displayed and to change the sizes may be provided. When the application range positions are moved or the sizes are changed by the input operation unit, the application range determining unit 32b resets the application ranges to the moved or changed positions and sizes, and then executes an iterative approximation projection data correction process again.

Figure 18:
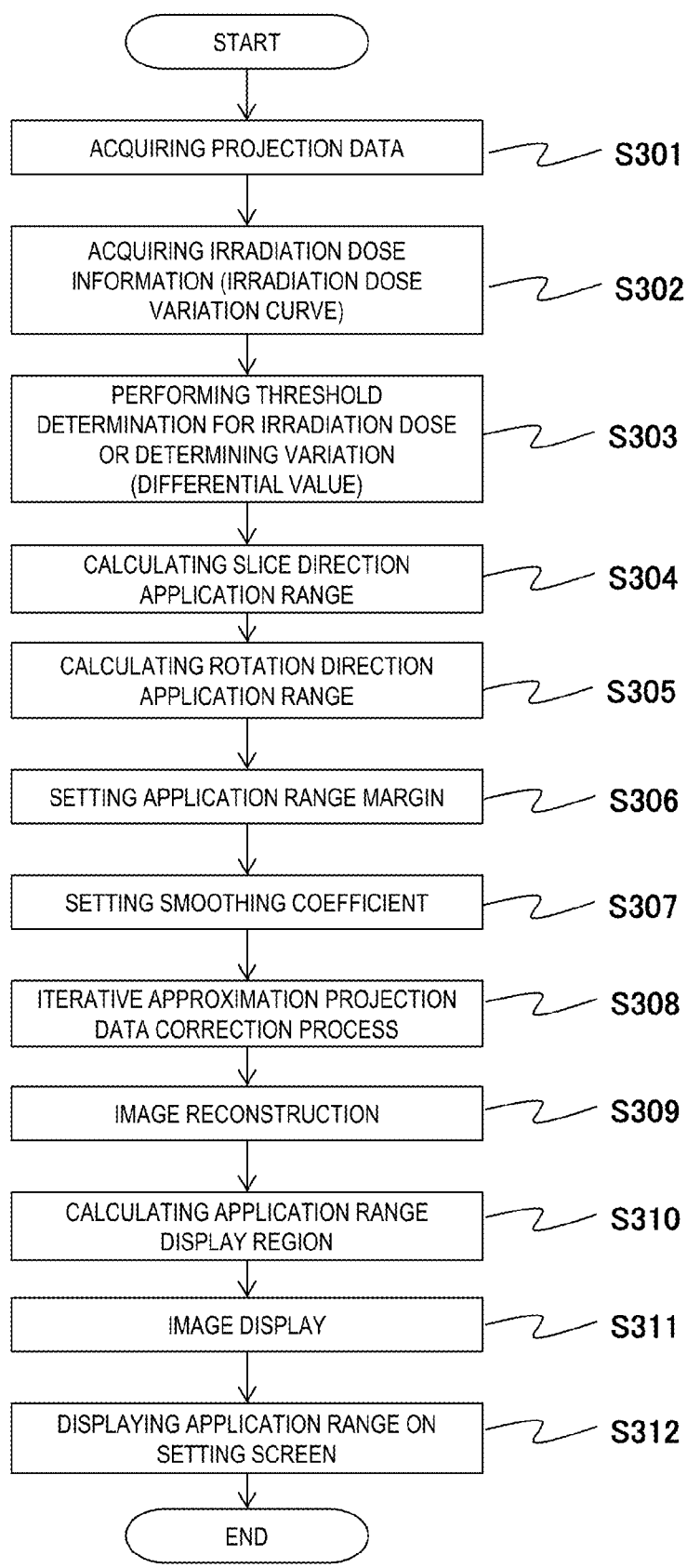
FIG. 18 is a flow chart showing the process flow in the second embodiment.

FIG. 18 is a flow chart explaining a process flow that the calculation device 202b of the second embodiment executes.

The calculation device 202b acquires projection data from the data collection device 106 (Step S301). The calculation device 202b (the application range determining unit 32b) acquires irradiation dose information (Step S302).

The calculation device 202b performs threshold determination for the acquired irradiation dose information or determines a variation (a derivative value) (Step S303). Then, based on the determination result, the slice direction application range 1001 is first calculated (Step S304). For example, the calculation device 202b calculates the slice direction application ranges 1001c, 1001d, and 1001e according to the irradiation dose change in a slice direction. A correction processing application range in the slice direction is expressed as a range of the index "j" for a position in the update formula.

As described above, a slice direction range in which an irradiation dose is smaller (or larger) than a predetermined threshold value is set as the slice direction application range 1001e. Alternatively, the slice direction application ranges 1001c and 1001d are determined according to whether there is a variation (a derivative value) of the irradiation dose.

Then, the calculation device 202b calculates a rotation direction application range (Step S305). The determination method of the rotation direction application range is the same as the slice direction application range 1001. For example, a rotation direction application range in which an irradiation dose is smaller (or larger) than a predetermined threshold value is set as the application range. Alternatively, the rotation direction application range is restricted according to whether there is a variation (a derivative value) of an irradiation dose. Also, because an irradiation dose is determined based on the electrocardiographic information acquired during scanning in electrocardiographic synchronous scanning, an optimal cardiac phase is set as the rotation direction application range 1003 on the basis of the characteristic waveform (for example, the R wave) of the irradiation dose.

The correction processing application ranges in the rotation direction are expressed as ranges of the index "i" for time in the update formula.

The process flow after Step S306 is the same as the processes after Step S205 of the first embodiment.

The calculation device 202b sets application range margins corresponding to each application range (Step S306). The calculation device 202b calculates a smoothing coefficient to be applied to the application range and the application range margins (Step S307). Next, the calculation device 202b applies the smoothing coefficient calculated in Step S307 to the application ranges and the application range margins determined in the processes from Step S304 to Step S306, and then performs an iterative approximation projection data correction process (Step S308).

The application ranges determined in Steps S304 and 305 are expressed as ranges of the indexes "i" and "j" included in the update formula (the above formula (4)) of the iterative approximation projection data correction process. Also, the smoothing coefficient determined in Step S307 corresponds to β included in the update formula. The calculation device 202b outputs projection data as a result of the iterative approximation projection data correction process and transmits it to the reconstruction processing device 221.

The reconstruction processing device 221 performs image reconstruction using the correction projection data corrected by an iterative approximation projection data correction process to generate a CT image (Step S309). Also, the calculation device 202b calculates display data for displaying an application range (Step S310). The calculation device 202b displays a generated CT image on the display device 211 (Step S311). Also, the calculation device 202b displays a range to which the iterative approximation projection data correction process is applied on the application range display screen 501b as shown in FIG. 14 (Step S312).

As described above, the calculation device 202b of the second embodiment restricts an application range for an iterative approximation projection data correction process in a slice direction and the rotation direction based on irradiation dose information in scanning with an optimal irradiation dose that performs scanning while changing an irradiation dose in a body-axis direction position or rotation direction position. Particularly, in cardiac scanning, a variation curve of the irradiation dose is generated based on electrocardiographic information. Therefore, a range for applying an iterative approximation projection data correction process based on the electrocardiographic information is restricted in a slice direction and the rotation direction. Hence, a processing time of the iterative approximation projection data correction process can be reduced. Also, because an application range for correction processing is displayed together with a positioning image, an image diagram, or electrocardiographic information, an operator can easily distinguish the application range for an iterative approximation projection data correction process. Hence, whether a noise-reduction image corresponding to the irradiation dose can be obtained or not can be clarified.

Third Embodiment

Next, referring to FIGS. 19 to 22, the third embodiment will be described in detail.

In the third embodiment, a method to calculate an application range for an iterative approximation projection data correction process based on ROI (Region of Interest) information set on an image by an operator will be described.

Figure 19:
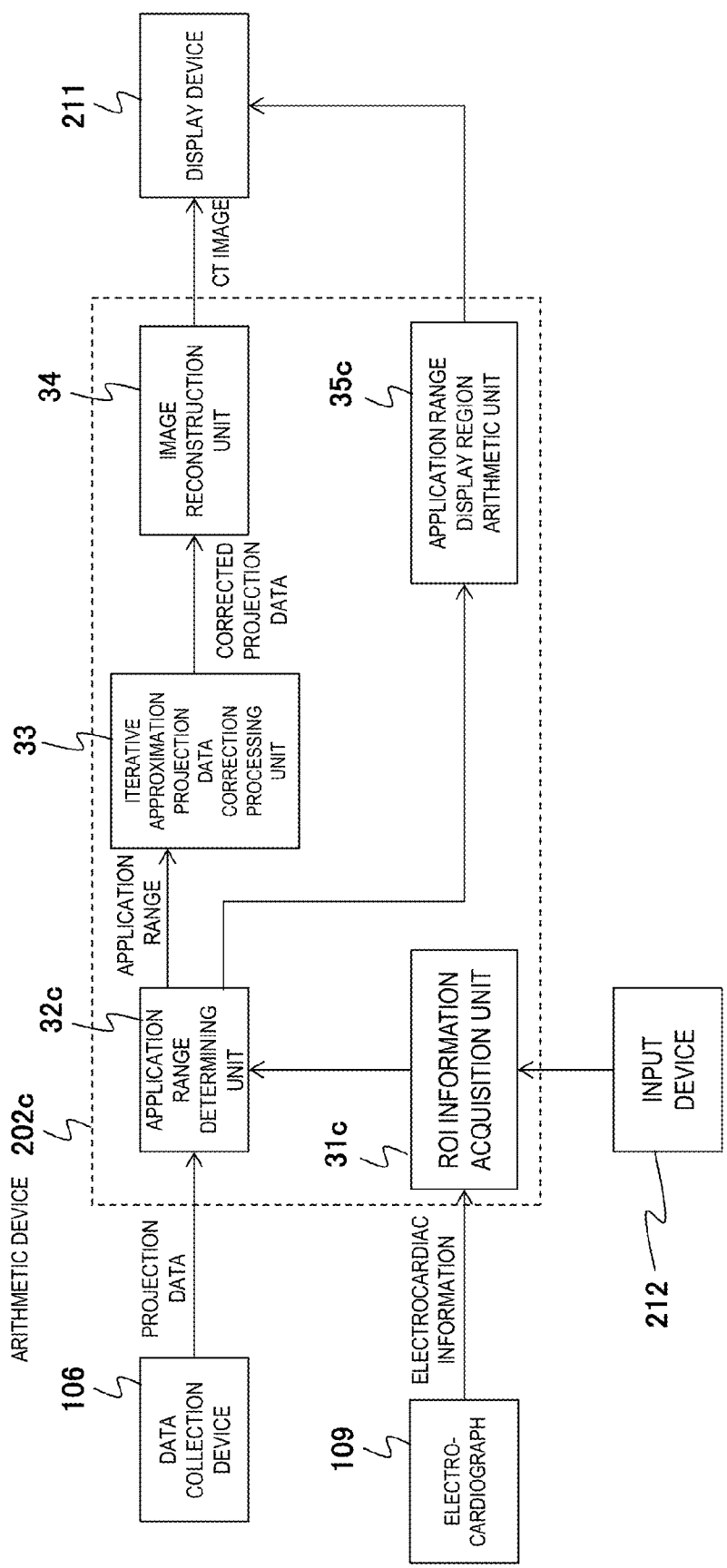
FIG. 19 is a functional block diagram of the calculation device 202c in the third embodiment.

FIG. 19 is a diagram showing the functional configuration of the calculation device 202c of the third embodiment.

In the third embodiment, the ROI information acquisition unit 31c is provided instead of the application range determining parameter acquisition unit 31 of the calculation device 202 shown in FIG. 3.

As shown in FIG. 19, the calculation device 202c of the third embodiment has the ROI information acquisition unit 31c, the application range determining unit 32c, the iterative approximation projection data correction processing unit 33, the image reconstruction unit 34, and the application range display region calculation unit 35c.

Additionally, the same symbols are used for the configuration elements similar to those shown in FIGS. 1, 2, and 3, and the repeated explanations are omitted. Also, although the calculation device 202c of the third embodiment is hardware similar to the calculation device 202 shown in FIG. 2, the symbols are different from the calculation device 202 in FIG. 2 due to the different functional configuration.

The ROI information acquisition unit 31c acquires ROI information as a parameter to determine an application range for an iterative approximation projection data correction process. The ROI information may be set on a CT image by an operator or may be set based on image analysis results. In the present embodiment, an example of determining a range of the iterative approximation projection data correction process based on the ROI information set on a CT image by an operator will be described.

Figure 20:
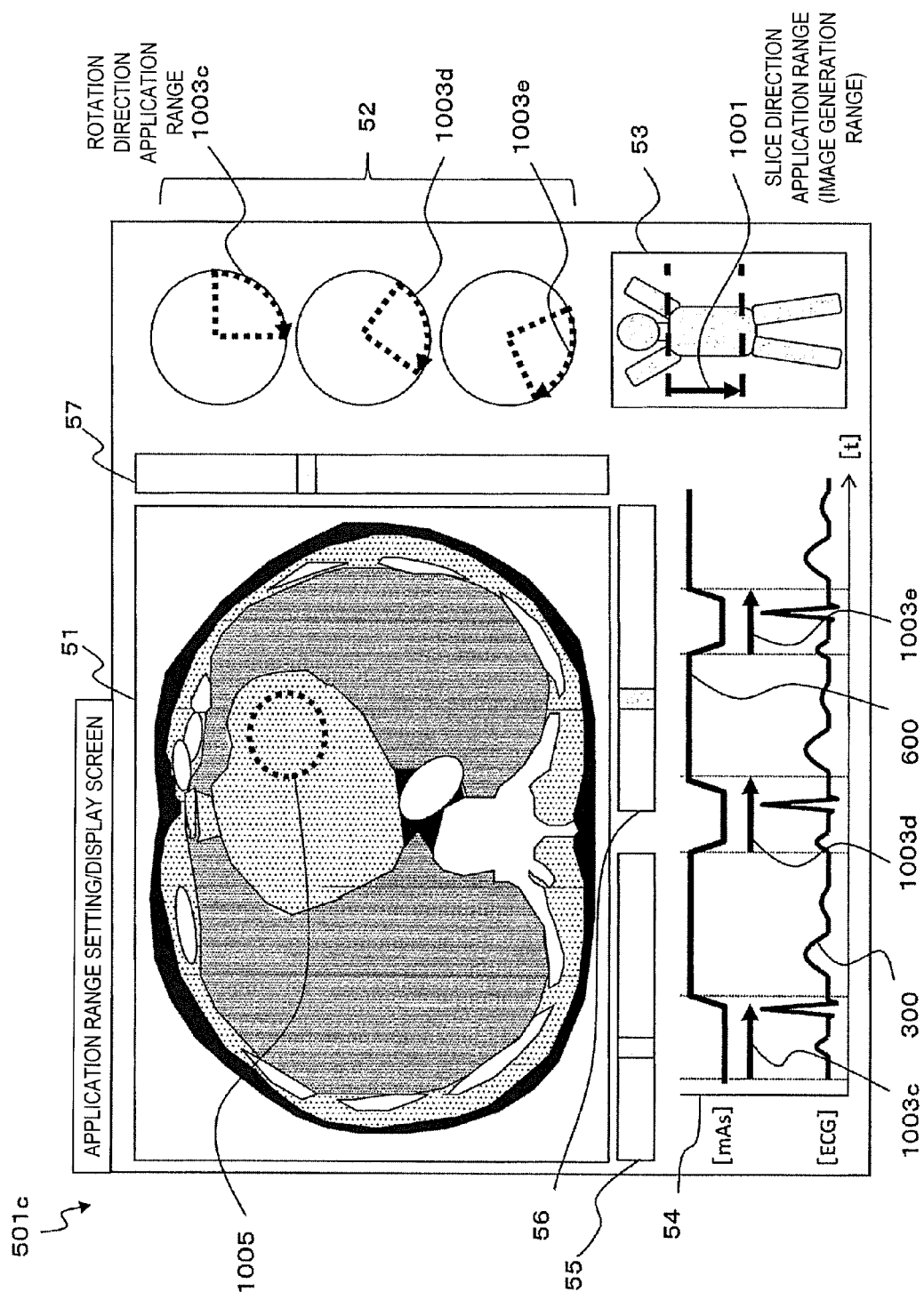
FIG. 20 is a diagram showing an example of the application range setting/display screen 501c in the third embodiment.

The ROI information acquisition unit 31c displays the application range setting/display screen 501c shown in FIG. 20 on the display device 211, for example. The application range setting/display screen 501c is an operation screen for which an operator sets an ROI and an application range for an iterative approximation projection data correction process.

The application range setting/display screen 501c shown in FIG. 20 will be described.

The application range setting/display screen 501c has the CT image display area 51, the rotation direction application range display area 52, the slice direction application range display area 53, the electrocardiographic information/irradiation dose information display area 54, the slide bars 55, 56, and 57, etc.

The CT image display area 51 displays a CT image generated based on projection data. Additionally, the CT image may be the original image (a CT image reconstructed based on projection data before correction processing) or may be a CT image reconstructed based on correction projection data for which an iterative approximation projection data correction process was performed. For example, the original image is displayed for the ROI setting immediately after scanning, and a CT image reconstructed based on correction projection data is displayed after the ROI setting. It is configured so that an operator can set an ROI (i.e., the application range 1005 for the iterative approximation projection data correction process) on a CT image.

The rotation direction application range display area 52 displays a rotation direction application range.

In the example of FIG. 20, a plurality of the channel direction application ranges 1003c, 1003d, and 1003e are set and displayed.

The body-axis direction application range display area 53 displays a positioning image and an image generation range in the body-axis direction. The image generation range is set as a reconstruction condition and is specified as the slice direction application range 1001 of an iterative approximation projection data correction process.

The electrocardiographic information/irradiation dose information display area 54 displays the electrocardiographic information 300 and the irradiation dose information (the irradiation dose variation curve) 600 along the same time axis. Also, the time direction (rotation direction) application ranges 1003c, 1003d, and 1003e of an iterative approximation projection data correction process are displayed along the same time axis as the time axis of the electrocardiographic information 300 and the irradiation dose information 600.

The slide bars 55 and 56 are operation areas for adjusting a position and size of an application range. For example, by adjusting the slide bar 55, the positions of the dotted lines and the arrows showing the time direction application ranges 1003 can be adjusted. Also, by adjusting the slide bar 56, the arrow lengths (dotted-line ranges) showing the time direction application ranges 1003 can be adjusted.

The slide bar 57 is an operation area for changing a cross-sectional position of an image to be displayed in the CT image display area 51.

In case of setting an ROI set by an operator to an application range for an iterative approximation projection data correction process, the ROI information acquisition unit 31c acquires an image generation range in the body-axis direction from the set reconstruction conditions. Also, an FOV is acquired corresponding to the ROI.

The application range determining unit 32c calculates application ranges in the body-axis direction (slice direction) and the channel direction based on ROI information to be input from the ROI information acquisition unit 31c.

The application range display region calculation unit 35c calculates display data so as to display a CT image and positioning image to be displayed on the above application range setting/display screen 501c or an application range in a range corresponding to irradiation dose information etc.

Figure 21:
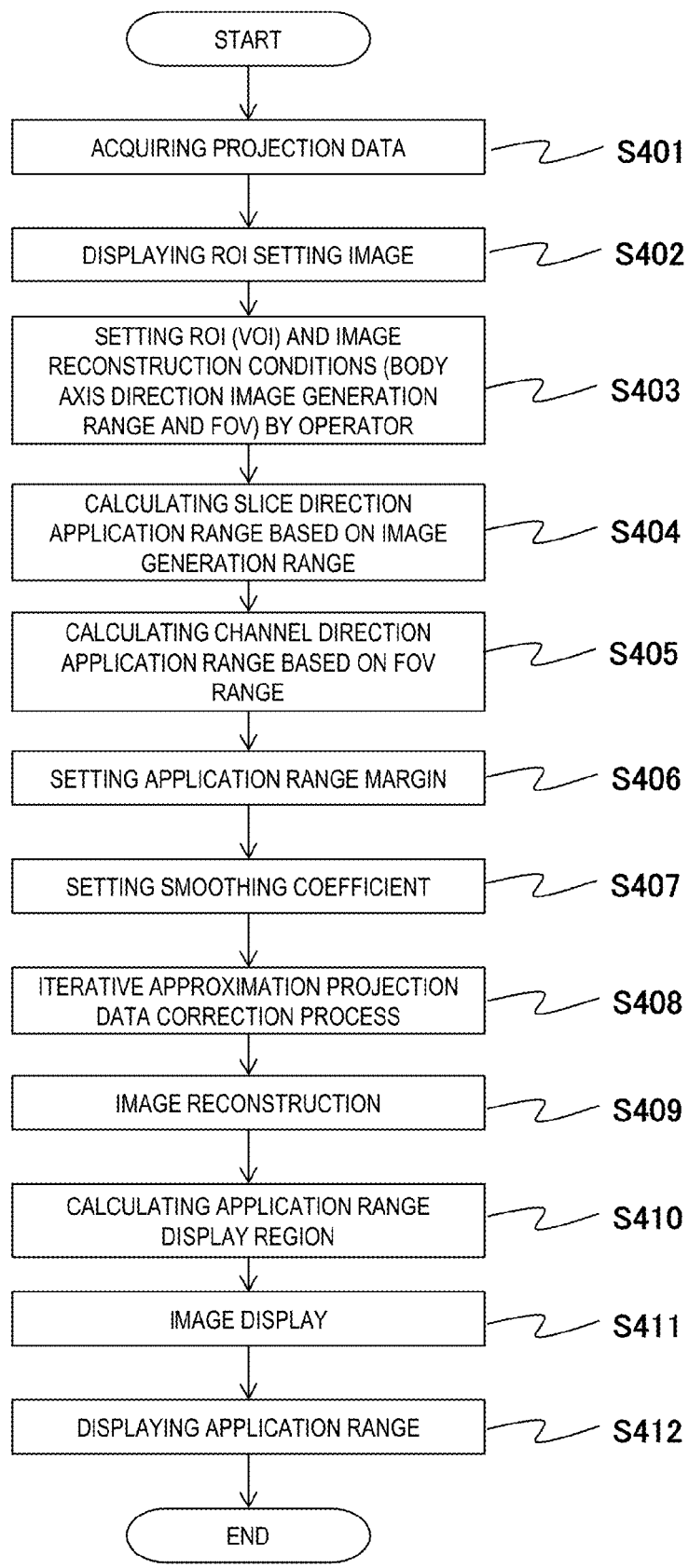
FIG. 21 is a flow chart showing the process flow in the third embodiment.

FIG. 21 is a flow chart explaining the process flow to be executed by the calculation device 202c of the third embodiment.

The calculation device 202c acquires projection data from the data collection device 106 (Step S401). Next, the calculation device 202c (the ROI information acquisition unit 31c) generates an ROI setting image based on the projection data to display on the above application range setting/display screen 501c (Step S402). After an operator sets an ROI and reconstruction conditions (Step S403), the calculation device 202c acquires an FOV corresponding to the image generation range in the body-axis direction and the ROI that were set. Additionally, on the above application range setting/display screen 501c, a VOI (Volume of Interest) in which a two-dimensional ROI is extended three-dimensionally may be able to be set.

The calculation device 202c calculates an application range in a slice direction based on the acquired image generation range (Step S404). Then, the calculation device 202c calculates a channel direction application range based on the acquired FOV range (Step S405). As shown in the setting screen of FIG. 20, the application range in a slice direction is set as the range corresponding to the image generation range input by an operator (the range of the symbol 1001 set in the body-axis direction application range display area 53).

Also, an application range may be determined not only for an iterative approximation projection data correction process according to the ROI information but also by referring to electrocardiographic information and irradiation dose information as shown in the second embodiment. In this case, the calculation device 202c determines the rotation direction application ranges 1003c, 1003d, and 1003e based on the electrocardiographic information and the irradiation dose information.

Thus, after setting a slice direction and an application range in the rotation direction, the calculation device 202 determines a range of the index "j" (a range for a position) of the update formula to be used for the calculation in an iterative approximation projection data correction process based on the slice direction application range. Similarly, a range of the index "i" for time is determined based on the rotation direction application range.

The process flow after Step S406 is the same as the processes after Step S205 of the first embodiment.

The calculation device 202c sets application margins corresponding to each application range (Step S406). The calculation device 202c calculates a smoothing coefficient to be applied to the application range and the application range margins (Step S407). Next, the calculation device 202c applies a smoothing coefficient calculated in Step S407 to the application range and the application range margins determined in the processes from Steps S404 to S406 and performs an iterative approximation projection data correction process (Step S408).

The application range determined in Steps S404 and S405 is expressed as the range of the indexes "i" and "j" included in the update formula (the above formula (4)) of an iterative approximation projection data correction process. Also, a smoothing coefficient corresponds to β included in the update formula. The calculation device 202c outputs correction projection data as a result of the iterative approximation projection data correction process and transmits the data to the reconstruction processing device 221.

The reconstruction processing device 221 performs image reconstruction using the correction projection data corrected by the iterative approximation projection data correction process to generate a CT image (Step S409). Also, the calculation device 202c calculates display data for displaying an application range (Step S410). The calculation device 202c displays the generated CT image on the display device 211 (Step S411). Also, the calculation device 202c displays a range to which the iterative approximation projection data correction process was applied on the application range setting/display screen 501c as shown in FIG. 20 (Step S412).

For example, the calculation device 202c displays the application range for the iterative approximation projection data correction process on the CT image display area 51 and displays the application range 1005 on the displayed CT image. Also, the calculation device 202c displays the rotation direction application ranges 1003c, 1003d, and 1003e respectively in the rotation direction application range display area 52 and the electrocardiographic information/irradiation dose information display area 54. Also, the calculation device 202c displays the slice direction application range 1001 in the slice direction application range display area 53.

As described above, when an ROI is set by an operator, the calculation device 202c restricts a range for applying an iterative approximation projection data correction process based on the ROI. Additionally, in cardiac scanning, a range to which an iterative approximation projection data correction process is applied based on electrocardiographic information is restricted in a slice direction and the rotation direction. Hence, the application range for an iterative approximation projection data correction process is restricted, which can reduce the processing time. Also, because the application range for the correction processing is displayed together with a positioning image, an image diagram, or electrocardiographic information, an operator can easily distinguish the application range. Hence, whether a noise-reduction image corresponding to the irradiation dose can be obtained in the specified ROI or not can be clarified.

Additionally, a plurality of ROIs may be set. A case of setting a plurality of ROIs will be described additionally.

In a case where a plurality of ROIs are set on the same CT image, it may be configured so that an application range corresponding to each ROI is provided. However, this makes the application range distribution complicated, and the calculation of an iterative approximation projection data correction process will be complicated. Additionally, in case of providing application range margins etc., a function showing a smoothing coefficient will be also complicated. Therefore, in a case where a plurality of ROIs are set on the same CT image, an ROI including the plurality of ROIs (hereinafter, referred to as a large ROI) is reset, and a range in a slice direction and channel direction corresponding to the reset large ROI may be set as an application range for an iterative approximation projection data correction process.

In the following description, an ROI set respectively is referred to as a small ROI, and a range including a plurality of small ROIs is referred to as a large ROI.

Figure 22:
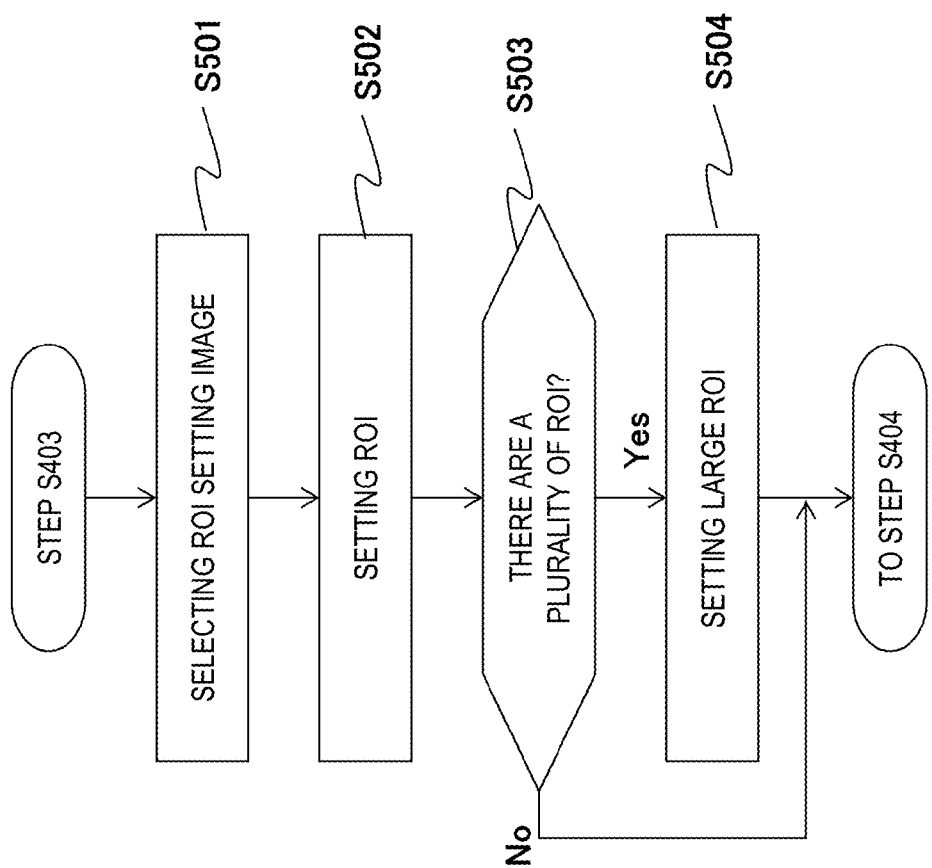
FIG. 22 is a flowchart explaining the details of ROI setting.

FIG. 22 is a flow chart explaining processes in a case where a plurality of small ROIs are set.

First, the calculation device 202c (the application range determining unit 32c) receives selection of an image to set an ROI. An operator adjusts the slide bar 57 on the setting screen to select a body-axis direction position of a CT image to be displayed on the CT image display area 51 (Step S501). On the selected CT image, ROIs (small ROIs) are set (Step S502). The small ROIs may overlap with each other or may be separated. Although the shapes of the small ROIs are desirably circular, they may also be the other shapes such as a rectangle and an ellipse.

In a case where a plurality of ROIs are set (Step S503: Yes), the calculation device 202c uses coordinate information of small ROIs set in Step S502 to calculate a region including all the small ROIs. This region is set as a large ROT (Step S504). The large ROI may include a region that an operator did not set as a small ROI. The shape of the large ROI is circular. Also, the large ROI is desirably set so that the center is close to the rotation center of scanning. This is because a region closer to the rotation center becomes an almost linear range on a sinogram and is easy to calculate an application range for an iterative approximation projection data correction process.

The processes after setting a large ROI are the same as those after the above Step S404. That is, the calculation device 202 acquires position information of the large ROI set by an operator and calculates a slice direction application range based on the acquired ROI information. Then, a channel direction application range is calculated. In a case where irradiation dose information etc. has already been acquired, a rotation direction application range is calculated. After setting the application ranges in the slice and channel directions, the calculation device 202 determines a range of the index "j" (a range for a position) of the update formula to be used for calculation in an iterative approximation projection data correction process based on the slice direction application range. Similarly, according to the rotation direction application range, a range of the index "i" for time is determined.

As described above, in the third embodiment, an application range for an iterative approximation projection data correction process can be restricted in the body-axis direction and channel direction based on an ROI set on a CT image by an operator. Also, in a case where irradiation dose information etc. have been acquired, an application range for an iterative approximation projection data correction process can be restricted in the rotation direction according to the irradiation dose information. Consequently, the processing time for the iterative approximation projection data correction process can be reduced. Also, the application range setting/display screen 501c displays an application range in each direction in a CT image or a positioning image and on an irradiation dose variation curve, etc. Therefore, an operator can easily distinguish the application range for the iterative approximation projection data correction process. Hence, whether a desired noise-reduction image is obtained in a desired range or not can be easily checked.

Additionally, in a case where a plurality of ROIs are set, an application range can be determined by setting one large ROI including the plurality of ROIs. This can prevent process complication and reduce the processing time. Hence, the usability and user-friendliness are improved, and the processing time can also be reduced.

Fourth Embodiment

Next, referring to FIGS. 23 to 25, the fourth embodiment will be described in details.

In the fourth embodiment, the method for calculating an application range for an iterative approximation projection data correction process based on variation information about moving organs will be described. The moving organs are the heart and the lungs, for example. In the following description, the heart will be described as an example.

The X-ray CT apparatus 1 calculates difference values between images with different time phases based on electrocardiographic information measured by the electrocardiograph 109 during scanning to calculate an image variation. Then, a time phase with a small image variation is set as an optimal cardiac phase, and a diagnostic image is reconstructed using projection data of the optimal cardiac phase. In the fourth embodiment, the optimal cardiac phase and the neighboring time range are set as an application range for an iterative approximation projection data correction process.

Figure 23:
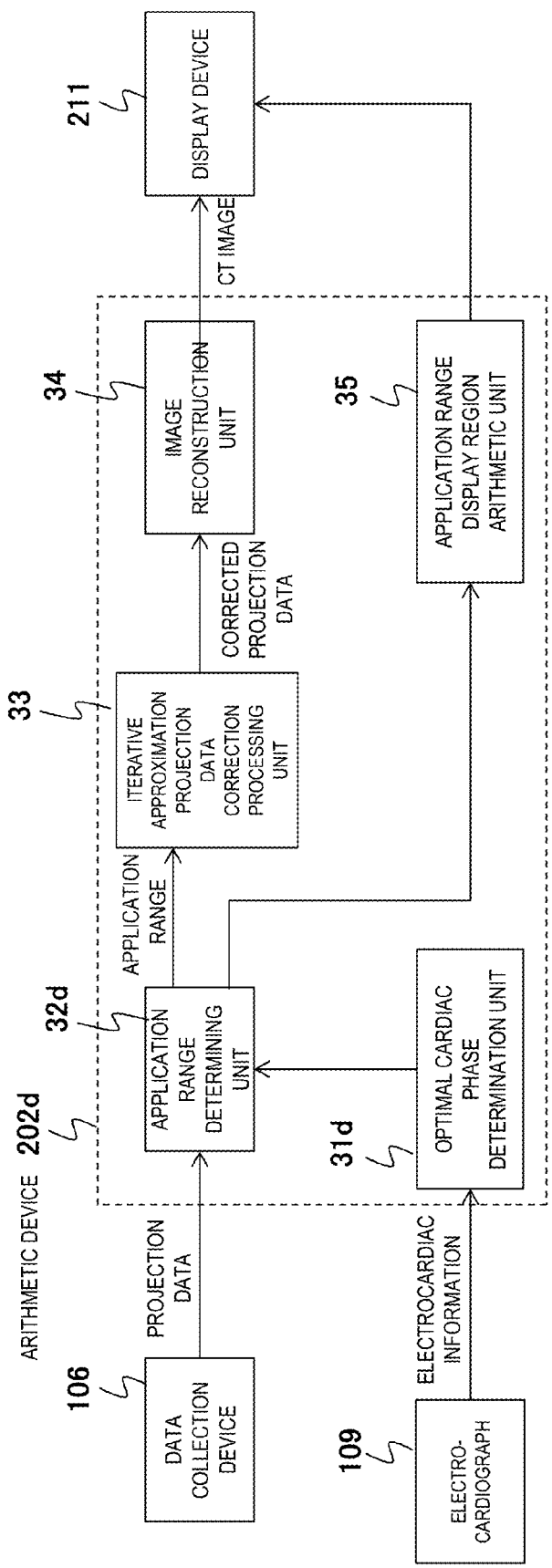
FIG. 23 is a functional block diagram of the calculation device 202d in the fourth embodiment.

FIG. 23 is a diagram showing the functional configuration of the calculation device 202d of the fourth embodiment.

In the fourth embodiment, the optimal cardiac phase determination unit 31d is provided instead of the application range determining parameter acquisition unit 31 of the calculation device 202 shown in FIG. 3.

As shown in FIG. 23, the calculation device 202d of the fourth embodiment has the optimal cardiac phase determination unit 31d, the application range determining unit 32d, the iterative approximation projection data correction processing unit 33, the image reconstruction unit 34, and the application range display region calculation unit 35.

Additionally, the same symbols are used for the configuration elements similar to those shown in FIGS. 1, 2, and 3, and the repeated explanations are omitted. Also, although the calculation device 202d of the fourth embodiment is hardware similar to the calculation device 202 shown in FIG. 2, the symbols are different from the calculation device 202 in FIG. 2 due to the different functional configuration.

The optimal cardiac phase determination unit 31d calculates difference values between images with different time phases based on electrocardiographic information. Then, variations between images in a target time phase are calculated from the sum of difference values. The optimal cardiac phase determination unit 31d sets a time phase whose variation between images is the smallest as an optimal cardiac phase, for example. Additionally, the optimal cardiac phase may be a time phase in which variations between images are the smallest values in all the phases or may be a time phase the respective variations between images are the smallest values in the expansion and contraction phases in light of the heart expansion/contraction.

Figure 24:
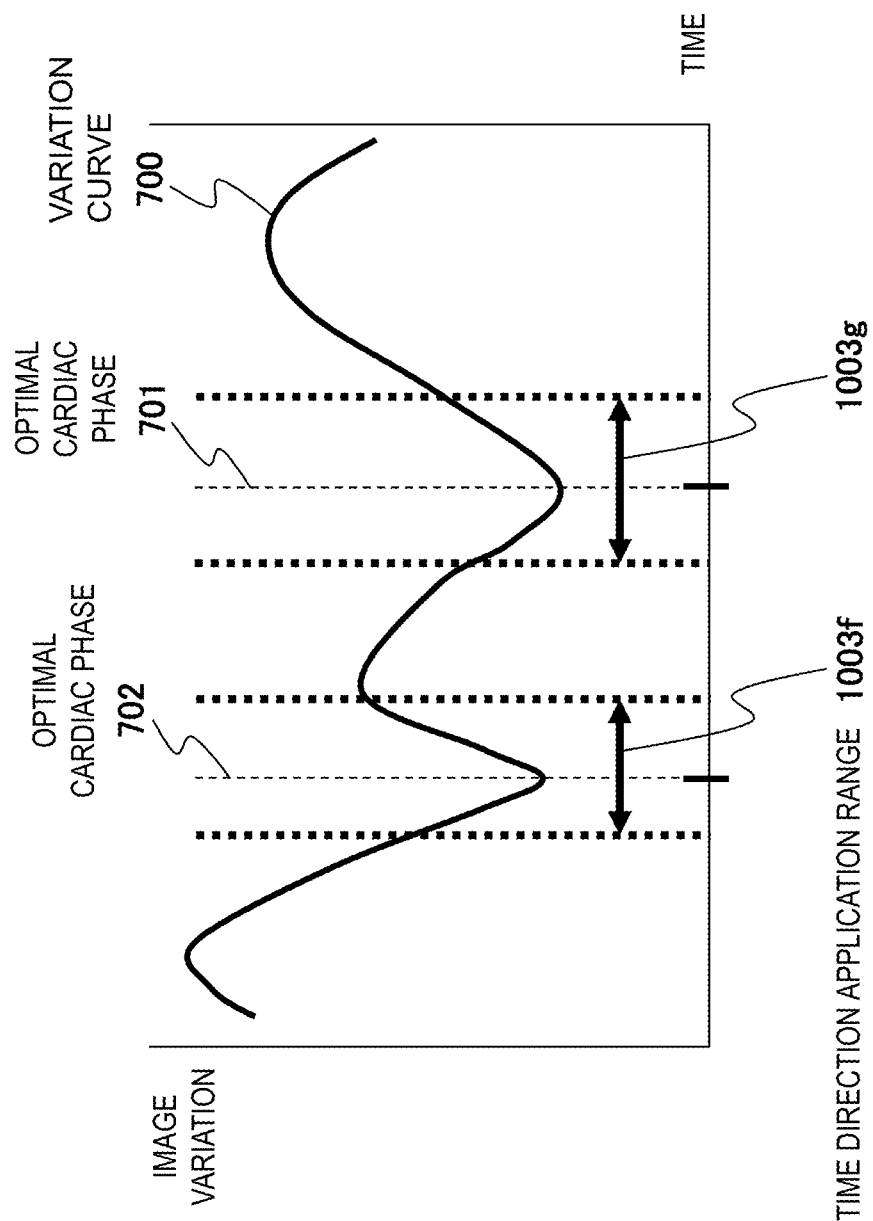
FIG. 24 is a diagram showing a relationship between optimal cardiac phases to be calculated from an image variation and a time direction application range.

FIG. 24 is a diagram showing an example of the variation curve 700 that shows an image variation change in each time phase.

The horizontal axis is the time phase (time), and the vertical axis is the image variation. By obtaining differences between images in neighboring time phases to calculate image variations, the variation transition can be found as shown in FIG. 24. Since motion artifacts do not appear so much in a time phase with a small image variation, the time phase is determined as an optimal cardiac phase, for example. In FIG. 24, the time phases 701 and 702 are set as optimal cardiac phases.

The application range determining unit 32d acquires optimal cardiac phase information determined by the optimal cardiac phase determination unit 31d. Then, a time-phase range including an optimal cardiac phase is set as the time direction (rotation direction) application range 1003 for an iterative approximation projection data correction process. As shown in FIG. 24, for example, a time-phase range in the vicinity of the optimal cardiac phase 702 is set as the time direction application range 1003f. Similarly, a time-phase range in the vicinity of the optimal cardiac phase 701 is set as the time direction application range 1003g.

Figure 25:
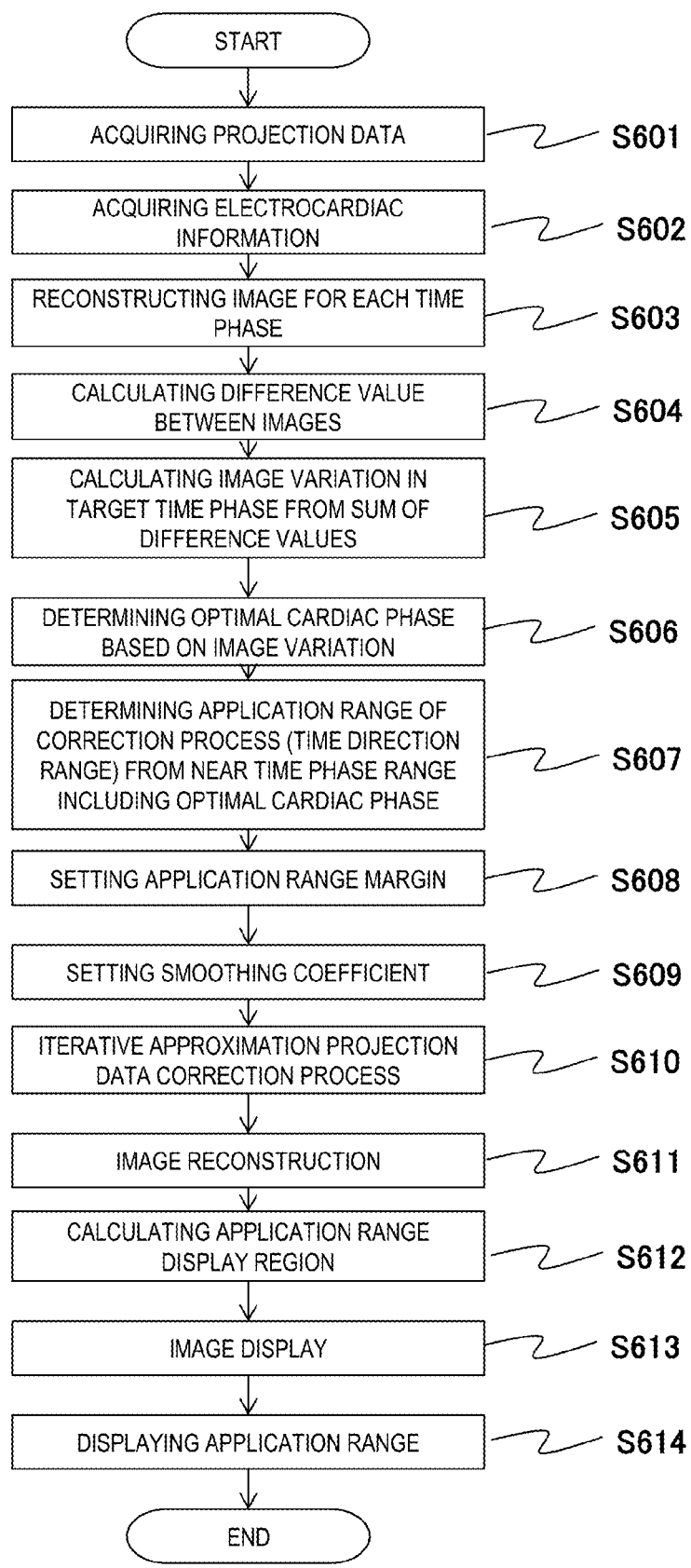
FIG. 25 is a flow chart showing the process flow in the fourth embodiment.

FIG. 25 is a flow chart explaining the process flow to be executed by the calculation device 202d of the fourth embodiment.

The calculation device 202d acquires projection data and electrocardiographic information (Step S601 and Step S602). The reconstruction processing device 221 reconstructs a CT image for each time phase based on the acquired projection data and electrocardiographic information (Step S603). The calculation device 202d (the optimal cardiac phase determination unit 31d) calculates difference values between images with different time phases (Step S604). Then, an image variation in a target phase is calculated from the sum of the difference values (Step S605). The calculation device 202d determines an optimal cardiac phase based on the image variation calculated in Step S605 (Step S606).

Then, the application range determining unit 32d (the calculation device 202d) acquires optimal cardiac phase information determined by the optimal cardiac phase determination unit 31d. The calculation device 202d sets a neighboring time-phase range including an optimal cardiac phase as the application ranges 1003f and 1003g for an iterative approximation projection data correction process (Step S607). The calculation device 202d determines a range of the index "i" (a range for time) of the update formula to be used for calculation in an iterative approximation projection data correction process based on the above application ranges 1003f and 1003g.

The process flow after Step S608 is the same as that after Step S205 of the first embodiment.

The calculation device 202d sets application range margins corresponding to each application margin (Step S608). The calculation device 202d calculates a smoothing coefficient to be applied to the application range and the application range margins (Step S609). Next, the calculation device 202d applies a smoothing coefficient calculated in Step S609 to the application range and the application range margins determined in the processes of Steps S607 to S608 and performs an iterative approximation projection data correction process (Step S610).

The application range determined in Step S607 is expressed as a range of the index "i" included in the update formula (the above formula (4)) of an iterative approximation projection data correction process. Also, a smoothing coefficient determined in Step S609 corresponds to β included in the update formula. The calculation device 202d outputs correction projection data as a result of the iterative approximation projection data correction process and transmits it to the reconstruction processing device 221.

The reconstruction processing device 221 performs image reconstruction using correction projection data corrected by an iterative approximation projection data correction process to generate a CT image (Step S611). Also, the calculation device 202d calculates display data to display an application range (Step S612). The calculation device 202d displays the generated CT image on the display device 211 (Step S613). Also, the calculation device 202d displays a range to which the iterative approximation projection data correction process was performed on the CT image, the setting screen, etc. (Step S614).

For example, the calculation device 202d displays an application range for an iterative approximation projection data correction process as shown in the rotation direction application range display area 52 of FIG. 20.

As described above, in the fourth embodiment, in case of scanning periodically moving organs, the calculation device 202d calculates an image variation and determines an optimal phase based on the image variation.

Then, a time-direction range in the vicinity of the time phase determined as the optimal phase is determined as an application range for an iterative approximation projection data correction process. Hence, an application range for correction processing can be restricted in the time direction (i.e., the rotation direction). Therefore, the processing time can be reduced.

Fifth Embodiment

Next, referring to FIGS. 26 to 27, the fifth embodiment will be described in detail.

In the fifth embodiment, an iterative approximation projection data correction process to an image for contrast-agent monitoring in contrast agent scanning will be described.

In the conventional CT examination using a contrast agent, contrast-agent monitor scanning is performed to monitor a contrast agent reaching a region of interest. In the contrast-agent monitor scanning, since whether the contrast agent has reached or not can be monitored in a predetermined monitoring position, scanning is performed at a low dose. In the fifth embodiment, an iterative approximation projection data correction process is performed also for projection data acquired for contrast-agent monitoring at a high speed by restricting a range. This improves image quality of an image for contrast-agent monitoring, which can perform highly accurate concentration monitoring.

Figure 26:
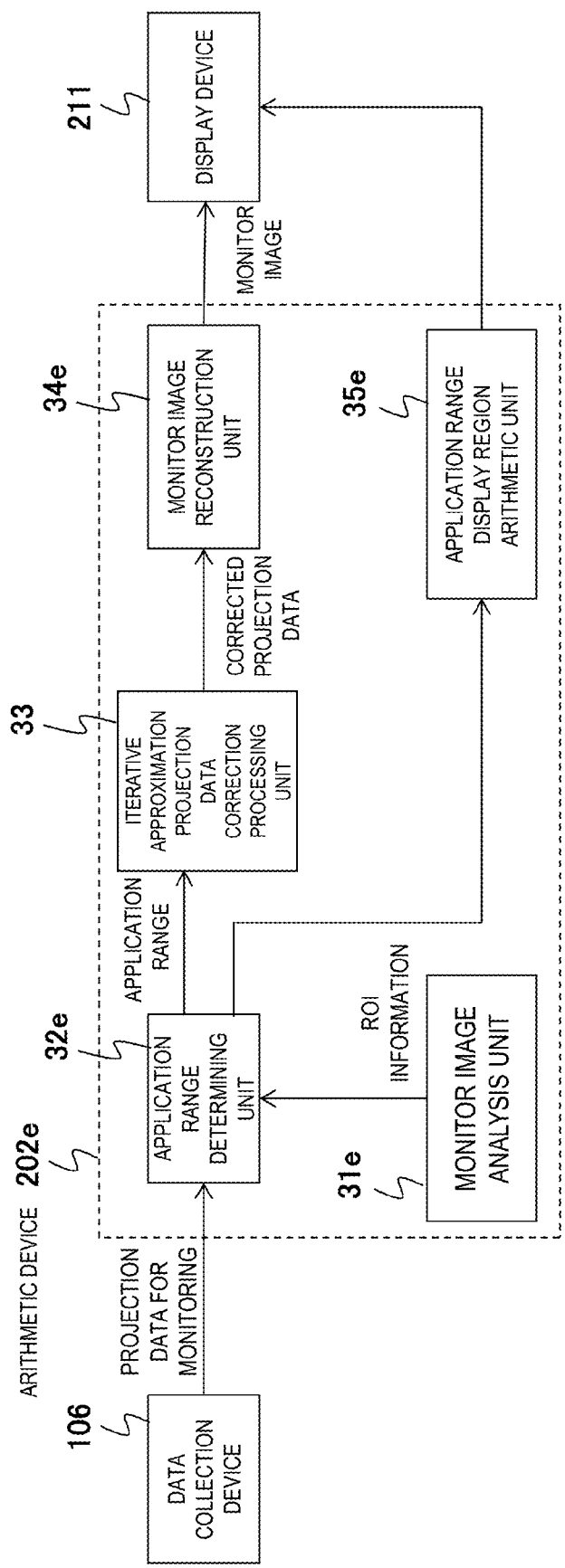
FIG. 26 is a functional block diagram of the calculation device 202e in the fifth embodiment.

FIG. 26 is a diagram showing the functional configuration of the calculation device 202e of the fifth embodiment.

In the fifth embodiment, the monitor image analysis unit 31e is provided instead of the application range determining parameter acquisition unit 31 of the calculation device 202 shown in FIG. 3.

As shown in FIG. 26, the calculation device 202e of the fifth embodiment has the monitor image analysis unit 31e, the application range determining unit 32e, the iterative approximation projection data correction processing unit 33, the monitor image reconstruction unit 34e, and the application range display region calculation unit 35e.

Additionally, the same symbols are used for the configuration elements similar to those shown in FIGS. 1, 2, and 3, and the repeated explanations are omitted. Also, although the calculation device 202e of the fifth embodiment is hardware similar to the calculation device 202 shown in FIG. 2, the symbols are different from the calculation device 202 in FIG. 2 due to the different functional configuration.

The monitor image analysis unit 31e acquires projection data for monitoring scanning (hereinafter, referred to as monitoring projection data) in a cross section to monitor a contrast agent concentration at each predetermined time. Then, a monitoring image is reconstructed immediately based on the monitoring projection data. The monitor image analysis unit 31e generates a time differential image between a monitoring image scanned last time and that scanned this time. The monitor image analysis unit 31e analyzes the inside of the generated time differential image. In the analysis, a region where relatively large difference values concentrate is searched in the time differential image. Then, an ROI is set so as to include a region where large difference values concentrate. The ROI set for the time differential image is specified as an ROI of a monitor image. The ROI setting is performed at each time of monitoring scanning.

The application range determining unit 32e acquires ROI information set by the monitor image analysis unit 31e. Based on the ROI information, the application range determining unit 32e performs the similar processes to the third embodiment for a monitor image. That is, the application range determining unit 32e, based on the ROI set by the monitor image analysis unit 31e, determines an application range for an iterative approximation projection data correction process for monitoring projection data. Application ranges in the body-axis direction (slice direction) and the channel direction are calculated.

The iterative approximation projection data correction processing unit 33e executes an iterative approximation projection data correction process by restricting to an application range determined by the application range determining unit 32e from among monitoring projection data.

The monitor image reconstruction unit 34e reconstructs a monitor image based on correction projection data input from the iterative approximation projection data correction processing unit 33. The monitor image reconstruction unit 34e outputs the reconstructed monitor image to the display device 211.

The application range display region calculation unit 35e performs calculation to display an application range determined by the application range determining unit 32e. For example, an application range position on a monitor image is calculated.

Figure 27:
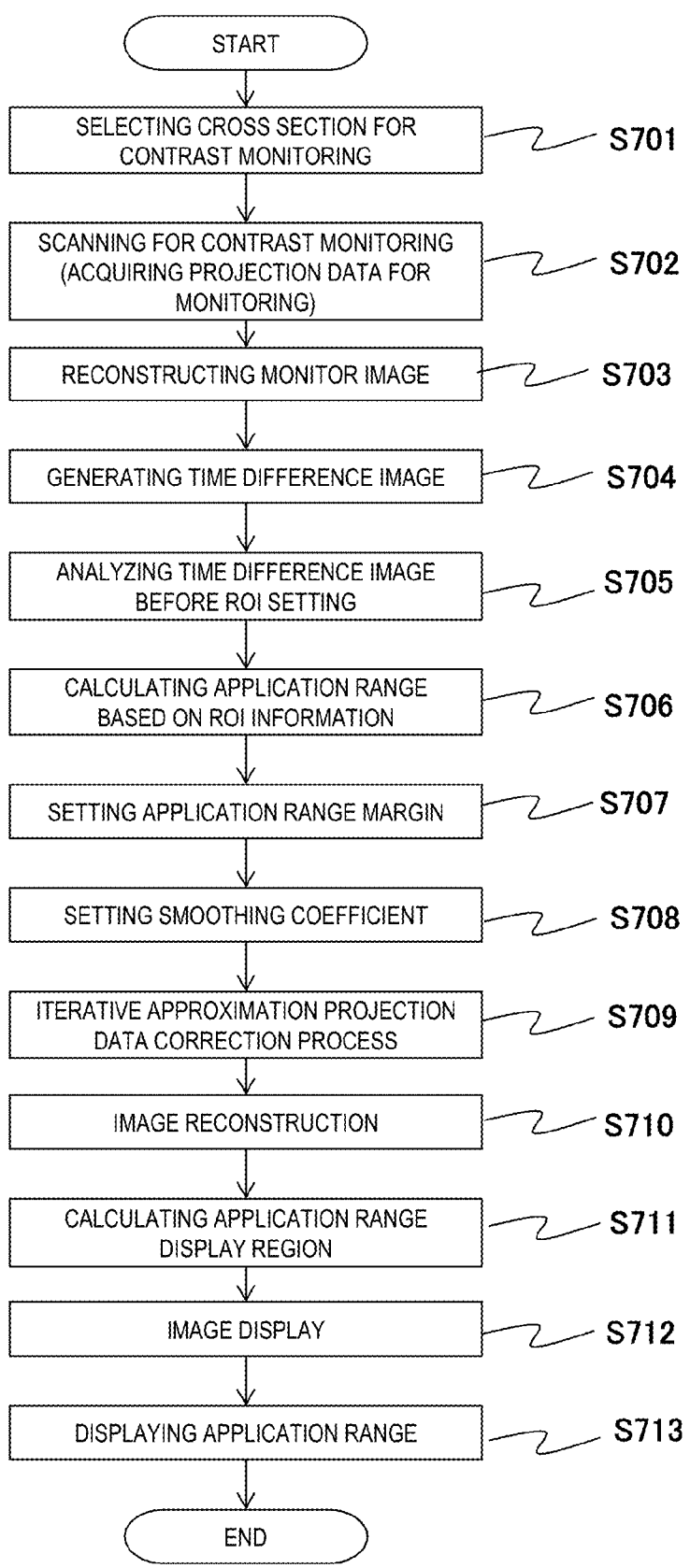
FIG. 27 is a flow chart showing the process flow in the fifth embodiment.

FIG. 27 is a flow chart explaining the process flow that the calculation device 202d executes of the fifth embodiment.

The calculation device 202e selects a cross section (for contrast monitoring) to monitor a contrast agent concentration (Step S701). Next, the calculation device 202e performs monitoring scanning for the cross section for contrast monitoring selected in Step S701 at each predetermined time (Step S702). The calculation device 202e (the monitor image analysis unit 31e) reconstructs a CT image using the monitoring projection data acquired by monitoring scanning for each time monitoring scanning is performed (Step S703).

The calculation device 202e further generates a time differential image between the image scanned last time and that scanned this time (Step S704). Also, the calculation device 202e (the monitor image analysis unit 31e) analyzes the time differential image generated in Step S702 for each monitoring scanning to set an ROI (Step S705). Here, the ROI is set so as to include a region where relatively large difference values concentrate in the time differential image.

The processes after Step S706 are the same as the process flow after setting an ROI in the third embodiment (the processes after Step S403 of FIG. 21).

The calculation device 202e calculates a slice direction application range and a channel direction application range for monitoring projection data based on the ROI information set in Step S705 (Step S706). After application ranges in the slice and channel directions are set, the calculation device 202 determines a range of the index "j" (a range for a position) of the update formula to be used for the calculation in an iterative approximation projection data correction process based on the slice direction application range. Similarly, a range of the index "i" for time is determined based on a rotation direction application range.

The calculation device 202e sets application range margins corresponding to each application range (Step S707). Also, the calculation device 202e calculates a smoothing coefficient to be applied to an application range and application range margins (Step S708). Next, the calculation device 202e applies a smoothing coefficient calculated in Step S708 to the application range and the application range margins determined in the process of Steps S706 to 707 and perform an iterative approximation projection data correction process (Step S709). The calculation device 202e outputs correction projection data as a result of the iterative approximation projection data correction process and transmits it to the reconstruction processing device 221.

The reconstruction processing device 221 performs image reconstruction using the correction projection data corrected by the iterative approximation projection data correction process to generate a monitor image (Step S710). Also, the calculation device 202e calculates display data to display an application range (Step S711).

The calculation device 202e displays the generated monitor image on the display device 211 (Step S712). Also, the calculation device 202e displays a range to which an iterative approximation projection data correction process was applied on the monitor image as shown in FIG. 11, for example (Step S713).

As described above, an iterative approximation projection data correction process can be performed for projection data acquired in contrast agent monitoring scanning during contrast scanning by restricting an application range. Therefore, image noise can be reduced on a contrast spot of a monitor image, which can perform highly accurate concentration monitoring in real time. Also, a monitoring image can be generated at a low dose by performing the iterative approximation projection data correction process, which can reduce an exposure dose.

Although the embodiments suitable for the X-ray CT apparatus and the image reconstruction method related to the present invention were described above, the present invention is not limited to the above embodiments. It is apparent that those skilled in the art can consider various changes or modifications within the technical ideas disclosed in the present application, and it is understood that these naturally belong to the technical scope of the present invention.

DESCRIPTION OF REFERENCE NUMERALS

1: X-ray CT apparatus, 3: object, 10: scanner, 20: operation unit, 100: gantry, 101: bed device, 102: X-ray generating device, 103: X-ray detection device, 104: collimator device, 105: high-voltage generating device, 106: data collection device, 107: driving device, 109: electrocardiograph, 200: central control device, 201: input/output device, 202: calculation device, 211: display device, 212: input device, 213: storage device, 221: reconstruction processing device, 222: image processing device, 31 and 31a: application range determining parameter acquisition unit, 31b: irradiation dose information acquisition unit, 31c: ROI information acquisition unit, 31d: optimal cardiac phase determination unit, 31e: monitor image analysis unit, 32 and 32a to 32e: application range determining unit, 33: an iterative approximation projection data correction processing unit, 34: image reconstruction unit, 34e: monitor image reconstruction unit, 35 and 35a to 35e: application range display region calculation unit, 4: FOV, 300: electrocardiogram, 501a and 501c: application range setting/display screen, 501b: application range display screen, 55, 56, and 57: slide bar (operation input unit), 600: irradiation dose variation curve, 601: positioning image, 700: image variation curve, 701 and 702: optimal cardiac phase, 1000 and 1000b: sinogram, 1001, 1001a, and 1001b: slice direction application range, 1002: channel direction application range, 1003 and 1003a to 1003g: rotation direction (time direction) application range, 2001 and 2001a to 2001c: slice direction application range margins, 2002: channel direction application range margins, 2003: rotation direction application range margins, 1005: application range boundary line, 2005: application range margin boundary line

The invention claimed is:

1. An X-ray CT apparatus comprising:
an X-ray generating device irradiating an X-ray from the surroundings of an object; an X-ray detection device detecting an X-ray transmitted through the object; a data collection device collecting data detected by the X-ray detection device; an calculation device generating projection data by inputting data to be collected by the data collection device and reconstructing a CT image using the projection data; and a display device displaying the CT image,
wherein the calculation device is comprised of:
an application range determining unit determining an application range for an iterative approximation projection data correction process that is a correction process by the iterative approximation method which uses a smoothing coefficient showing a correction intensity for the projection data;
an iterative approximation projection data correction processing unit performing the iterative approximation projection data correction process for projection data that corresponds to the range determined by the application range determining unit to generate correction projection data; and
an image reconstruction unit reconstructing a CT image using the correction projection data,
wherein margin regions are set around a range determined by the application range determining unit, and the iterative approximation projection data correction process is performed for projection data corresponding to the margin regions by changing the smoothing coefficient continuously.

2. The X-ray CT apparatus according to claim 1, wherein an application range display unit displaying an application range for the iterative approximation projection data correction process on the CT image is further included.

3. The X-ray CT apparatus according to claim 1, wherein the application range determining unit determines a range to apply the iterative approximation projection data correction process based on at least one of scanning condition information, the X-ray irradiation dose information, and image reconstruction condition information.

4. The X-ray CT apparatus according to claim 1, further comprising:
an input unit receiving input of scanning condition information or image reconstruction condition information,
wherein the application range determining unit determines a range to apply the iterative approximation projection data correction process based on the input scanning condition information or the input image reconstruction condition information.

5. The X-ray CT apparatus according to claim 1, further comprising:
an input unit receiving ROI setting on a CT image,
wherein the application range determining unit determines a range to apply the iterative approximation projection data correction process based on the set ROI.

6. The X-ray CT apparatus according to claim 1, wherein the application range determining unit determines a range to apply the iterative approximation projection data correction process based on the ROI set on a CT image.

7. The X-ray CT apparatus according to claim 1, further comprising:

a scanning unit for contrast monitoring that performs scanning for contrast monitoring to monitor contrast agent reaching in scanning using a contrast agent, wherein the calculation unit determines a range in which an iterative approximation projection data correction process is applied to monitoring projection data acquired in scanning for contrast monitoring by the application range determining unit and includes a monitor image reconstruction unit that reconstructs a CT image for monitoring using the correction projection data acquired by performing the iterative approximation projection data correction process for the monitoring projection data corresponding to the determined range.

8. The X-ray CT apparatus according to claim 1,
wherein the application range determining unit restricts a range to which the iterative approximation projection data correction process is applied in at least any one of the body-axis direction, the channel direction, and the time direction from among all the ranges of the projection data.

9. The X-ray CT apparatus according to claim 1,
wherein the application range display unit displays an application range for the iterative approximation projection data correction process together with the margin regions.

10. The X-ray CT apparatus according to claim 1,
wherein an operation screen display unit displaying an operation screen for adjusting a range to apply the iterative approximation projection data correction process is further included.

11. An X-ray CT apparatus comprising:
an X-ray generating device irradiating an X-ray from the surroundings of an object; an X-ray detection device detecting an X-ray transmitted through the object; a data collection device collecting data detected by the X-ray detection device; an calculation device generating projection data by inputting data to be collected by the data collection device and reconstructing a CT image using the projection data; and a display device displaying the CT image, wherein the calculation device is comprised of:
an application range determining unit determining an application range for an iterative approximation projection data correction process that is a correction process by the iterative approximation method which uses a smoothing coefficient showing a correction intensity for the projection data;

an iterative approximation projection data correction processing unit performing the iterative approximation projection data correction process for projection data that corresponds to the range determined by the application range determining unit to generate correction projection data;

an image reconstruction unit reconstructing a CT image using the correction projection data, wherein the application range determining unit determines a range to apply the iterative approximation projection data correction process based on the ROI set on a CT image, and wherein the application range determining unit sets one large ROI including a plurality of ROIs and determines an application range for the iterative approximation projection data correction process based on the large ROI.

12. An X-ray CT apparatus comprising:
an X-ray generating device irradiating an X-ray from the surroundings of an object; an X-ray detection device detecting an X-ray transmitted through the object; a data collection device collecting data detected by the X-ray detection device; an calculation device generating projection data by inputting data to be collected by the data collection device and reconstructing a CT image using the projection data; and a display device displaying the CT image, wherein the calculation device is comprised of:
an application range determining unit determining an application range for an iterative approximation projection data correction process that is a correction process by the iterative approximation method which uses a smoothing coefficient showing a correction intensity for the projection data;

an iterative approximation projection data correction processing unit performing the iterative approximation projection data correction process for projection data that corresponds to the range determined by the application range determining unit to generate correction projection data;

an image reconstruction unit reconstructing a CT image using the correction projection data; and a measurement unit measuring information about periodic movement of organs during scanning, wherein the application range determining unit calculates a periodic variation of an image based on the information about the periodic movement of organs measured by the measurement unit, determines an optimal time phase for reconstruction based on the calculated variation, and then sets a time range including the determined time phase as a range to which the iterative approximation projection data correction process is applied.

13. An image reconstruction method of using a smoothing coefficient showing a correction intensity to create correction projection data by performing correction processing for projection data by the iterative approximation method and reconstructing a CT image using the correction projection data, wherein an calculation device performs:
an application range determination step of determining a range in which correction processing by the iterative approximation method is applied to the projection data, and a correction projection data creation step of performing correction processing by the iterative approximation method for projection data corresponding to the determined range and creating correction projection data wherein margin regions are set around a range determined by the application range determining step, and the iterative approximation projection data correction process is performed for projection data corresponding to the margin regions by changing the smoothing coefficient continuously.

* * * * *